United States Patent
Kalafut et al.

(10) Patent No.: US 11,331,056 B2
(45) Date of Patent: May 17, 2022

(54) COMPUTED TOMOGRAPHY MEDICAL IMAGING STROKE MODEL

(71) Applicants: GE Precision Healthcare LLC, Milwaukee, WI (US); Partners HealthCare System, Inc., Boston, MA (US); The General Hospital Corporation, Boston, MA (US); The Brigham and Women's Hospital, Inc., Boston, MA (US)

(72) Inventors: John Francis Kalafut, Pittsburgh, PA (US); Bernardo Bizzo, Boston, MA (US); Romane Gauriau, Boston, MA (US); Michael Lev, Boston, MA (US); Mark Heinz Michalski, Boston, MA (US)

(73) Assignees: GE PRECISION HEALTHCARE LLC, Milwaukee, WI (US); PARTNERS HEALTHCARE SYSTEM, INC., Boston, MA (US); THE GENERAL HOSPITAL CORPORATION, Boston, MA (US); THE BRIGHAM AND WOMEN'S HOSPITAL INC., Boston, MA (US)

( * ) Notice: Subject to any disclaimer, the term of this patent is extended or adjusted under 35 U.S.C. 154(b) by 239 days.

(21) Appl. No.: 16/588,013

(22) Filed: Sep. 30, 2019

(65) Prior Publication Data
US 2021/0093258 A1 Apr. 1, 2021

(51) Int. Cl.
*A61B 6/03* (2006.01)
*G06N 20/00* (2019.01)
(Continued)

(52) U.S. Cl.
CPC .............. *A61B 6/032* (2013.01); *A61B 6/501* (2013.01); *A61B 6/504* (2013.01); *G06N 3/08* (2013.01);
(Continued)

(58) Field of Classification Search
CPC ......... A61B 6/032; A61B 6/501; A61B 6/504; A61B 6/507; G06N 20/00; G06N 3/08; G06T 2207/10081; G06T 2207/30016
(Continued)

(56) References Cited

U.S. PATENT DOCUMENTS

2002/0196965 A1* 12/2002 Wallace ................ G06T 7/0012
382/131
2009/0034812 A1 2/2009 Nowinski et al.
(Continued)

OTHER PUBLICATIONS

Pedemonte et al., "Detection and Delineation of Acute Cerebral Infarct on DWI using Weakly Supervised Machine Learning," Medical Image Computing and Computer Assisted Intervention—MICCAI, 2018, 8 pages.
(Continued)

*Primary Examiner* — Michael R Neff
(74) *Attorney, Agent, or Firm* — Amin, Turocy & Watson, LLP

(57) ABSTRACT

Systems and techniques for generating and/or employing a computed tomography (CT) medical imaging stroke model are presented. In one example, a system employs a convolutional neural network to generate learned medical imaging stroke data regarding a brain anatomical region based on CT data associated with the brain anatomical region and diffusion-weighted imaging (DWI) data associated with one or more segmentation masks for the brain anatomical region.
(Continued)

The system also detects presence or absence of a medical stroke condition in a CT image based on the learned medical imaging stroke data.

17 Claims, 11 Drawing Sheets

(51) Int. Cl.
    *A61B 6/00*     (2006.01)
    *G06N 3/08*     (2006.01)

(52) U.S. Cl.
    CPC .............. *G06N 20/00* (2019.01); *A61B 6/507* (2013.01); *G06T 2207/10081* (2013.01); *G06T 2207/30016* (2013.01)

(58) Field of Classification Search
    USPC ......................................................... 382/131
    See application file for complete search history.

(56) References Cited

U.S. PATENT DOCUMENTS

| | | | |
|---|---|---|---|
| 2016/0035085 A1* | 2/2016 | Peng | G06T 7/136 382/128 |
| 2016/0180042 A1* | 6/2016 | Menon | A61B 5/0042 705/2 |
| 2018/0218497 A1* | 8/2018 | Golden | G06T 7/11 |
| 2018/0268942 A1 | 9/2018 | Kamali-Zare et al. | |
| 2019/0021677 A1* | 1/2019 | Grbic | A61B 5/7292 |
| 2019/0026888 A1* | 1/2019 | Beveridge | A61B 6/037 |

OTHER PUBLICATIONS

Non-Final Office Action received for U.S. Appl. No. 16/588,080 dated Dec. 24, 2021, 42 pages.

* cited by examiner

COMPUTED TOMOGRAPHY MEDICAL IMAGING STROKE MODEL

TECHNICAL FIELD

This disclosure relates generally to machine learning and/or artificial intelligence related to medical imaging.

BACKGROUND

A medical imaging device such as a computed tomography (CT) device is often employed to generate medical images to facilitate detection and/or diagnosis of a medical condition for a patient. For example, a CT scan can be performed to acquire medical images regarding an anatomical region to facilitate detection and/or diagnosis of a medical condition associated with the anatomical region. However, using human analysis to analyze CT images for the presence of a certain medical condition such as, for example, an ischemic stroke, is generally difficult and/or time consuming. Furthermore, human analysis of CT images is error prone. As such, conventional medical imaging techniques can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system comprises a memory that stores computer executable components. The system also comprises a processor that executes the computer executable components stored in the memory. The computer executable components comprise a machine learning component and a medical diagnosis component. The machine learning component employs a convolutional neural network to generate learned medical imaging stroke data regarding a brain anatomical region based on computed tomography (CT) data associated with the brain anatomical region and diffusion-weighted imaging (DWI) data associated with one or more segmentation masks for the brain anatomical region. The medical diagnosis component detects presence or absence of a medical stroke condition in a CT image based on the learned medical imaging stroke data.

According to another embodiment, a method is provided. The method provides for employing, by a system comprising a processor, a convolutional neural network to generate learned medical imaging stroke data regarding a brain anatomical region based on computed tomography (CT) data associated with the brain anatomical region and diffusion-weighted imaging (DWI) data associated with one or more segmentation masks for the brain anatomical region. The method also provides for detecting, by the system, presence or absence of a medical stroke condition in a CT image based on the learned medical imaging stroke data.

According to yet another embodiment, a computer readable storage device comprising instructions that, in response to execution, cause a system comprising a processor to perform operations. The operations comprise generating, using a convolutional neural network, learned medical imaging stroke data regarding a brain anatomical region based on computed tomography (CT) data associated with the brain anatomical region and diffusion-weighted imaging (DWI) data associated with one or more segmentation masks for the brain anatomical region. The operations also comprise detecting presence or absence of a medical stroke condition associated with a CT image based on the learned medical imaging stroke data.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
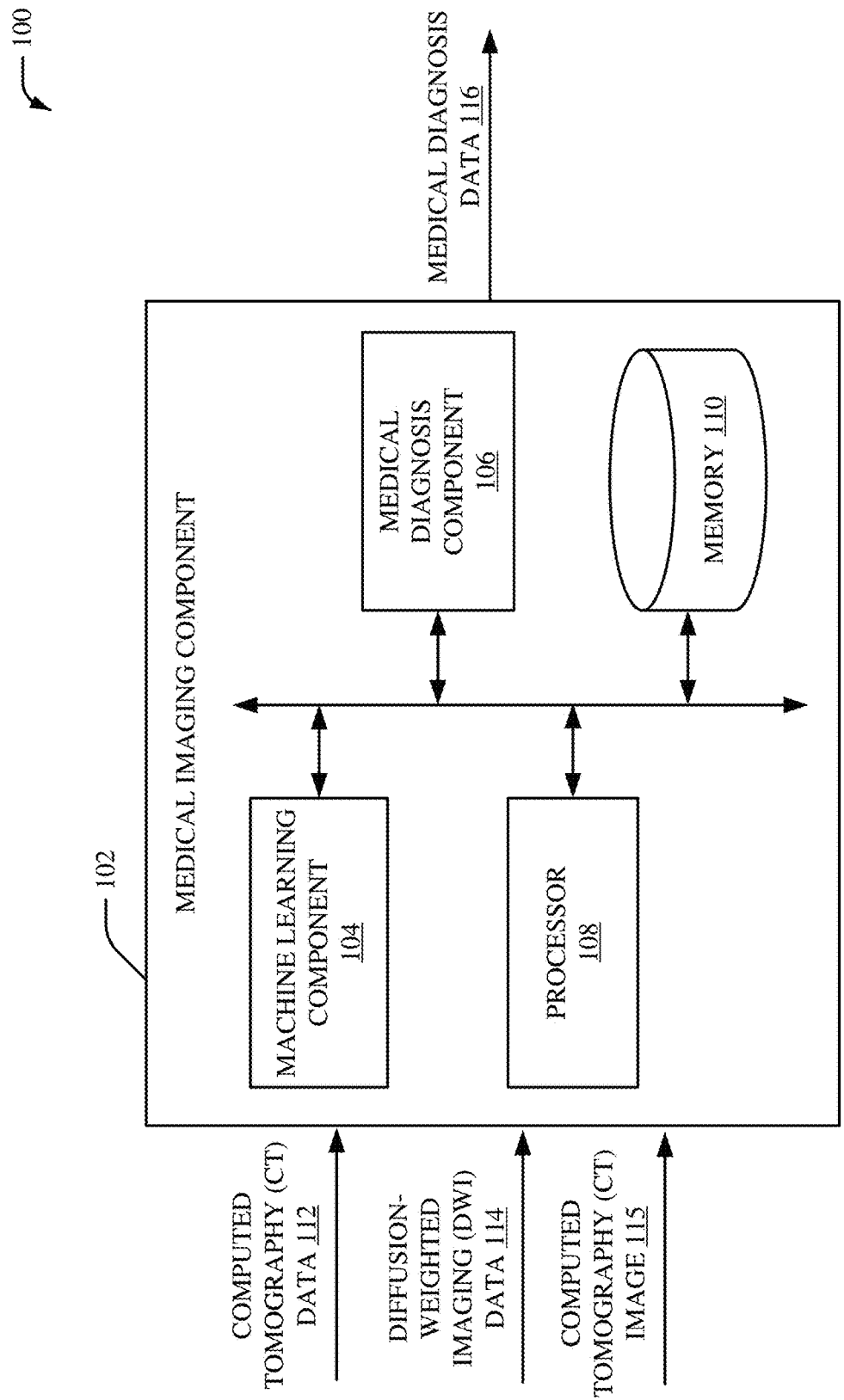
FIG. 1 illustrates a high-level block diagram of an example medical imaging component, in accordance with one or more embodiments described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for generating and/or employing a computed tomography (CT) medical imaging stroke model are presented. For instance, a deep learning architecture can be provided to facilitate detection of a medical stroke condition (e.g., an ischemic stroke, an arterial ischemic stroke, an infarct, etc.) based on CT data of a brain anatomical region and magnetic resonance imaging (MRI) data associated with one or more segmentation masks of the brain anatomical region. It is to be appreciated that, in an alternate embodiment, the deep learning architecture can be provided to facilitate detection of another type of neuro-defect based on the CT data and the MRI data. In an aspect, prior-acquired data (e.g., prior-acquired MRI data and/or prior-acquired CT data) can be employed to build and/or train a machine learning model using one or more deep learning techniques. Furthermore, the trained machine learning model can process CT data at "run-time" to make an inference of a medical stroke condition (e.g., an ischemic stroke, an arterial ischemic stroke, an infarct, etc.) associated with a brain anatomical region. In another aspect, the deep learning architecture can employ the CT data and diffusion-weighted imaging (DWI) data associated with one or more segmentation masks of the brain anatomical region to facilitate detection of a medical stroke condition (e.g., an ischemic stroke, an arterial ischemic stroke, an infarct, etc.). For instance, the deep learning architecture can employ the CT data and MRI DWI data to facilitate detection of a medical stroke condition (e.g., an ischemic stroke, an arterial ischemic stroke, an infarct, etc.). In an embodiment, the CT data and the MRI data (e.g., the DWI data, the DWI MRI data, etc.) can be employed to train a convolutional neural network of the deep learning architecture. In certain embodiments, the CT data and the MRI data (e.g., the DWI data, the DWI MRI data, etc.) can both be acquired within a certain time frame (e.g., within 3 hours or less). For instance, the CT data can be acquired by one or more CT scanner devices. Furthermore, within a certain time frame (e.g., within 3 hours or less) after the CT data is acquired by the one or more CT scanner devices, the MRI data (e.g., the DWI data, the DWI MRI data, etc.) can be acquired by one or more MRI scanner devices. In certain embodiments, the one or more CT scanner devices and the one or more MRI scanner devices can be located at different physical facilities, but corresponding CT data and MRI data can be associated with the same person. The convolutional neural network of the deep learning architecture can be trained based on the CT data and the MRI data (e.g., the DWI data, the DWI MRI data, etc.) to generate learned medical imaging stroke data. The learned medical imaging stroke data can include, for example, one or more segmentations regarding presence of a medical stroke condition (e.g., an ischemic stroke, an arterial ischemic stroke, an infarct, etc.) in a brain anatomical region. In certain embodiments, training data can be provided to the convolutional neural network of the deep learning architecture in the form of a cohort pair of axial MRI DWI data and non-contrast CT (NCCT) images.

In another embodiment, the learned medical imaging stroke data can be employed for medical diagnosis purposes associated with a patient. For example, a CT image of a brain anatomical region of a patient can be provided to a trained version of the convolutional neural network of the deep learning architecture (e.g., a version of the convolutional neural network of the deep learning architecture that is trained based on the CT data and the MRI data). Furthermore, the trained version of the convolutional neural network can detect presence or absence of a medical stroke condition in the CT image. In certain embodiments, the deep learning architecture can determine an outline of an infarct core associated with the brain anatomical region. An infarct can be an area of necrosis resulting from lack of blood supply to the area of the brain anatomical region. In another embodiment, the deep learning architecture can provide a label indicating presence of medical stroke condition and/or a segmentation (e.g., a contour outline) of a core region of the medical stroke condition. In an aspect, the deep learning architecture can employ a convolutional neural network (e.g., an adapted U-net model, a three-dimensional U-net model, etc.) to generate segmentation output for the detection of the medical stroke condition. In certain embodiments, a text output can be provided to a user device to indicate presence or absence of the medical stroke condition. As such, by employing systems and/or techniques associated with the medical imaging stroke model disclosed herein, MRI-type performance can be achieved by employing CT input data. For instance, by employing systems and/or techniques associated with the medical imaging stroke model disclosed herein, diagnosis speed and/or accuracy for a medical condition can be improved. A treatment decision for a medical condition can also be improved. For instance, a treatment decision for a medical condition can also be improved by employing outputs and/or classifications of one or more trained machine learning models to notify clinical care in less time as compared to a scenario where distributed teams of human physicians are used to interpret medical imaging data. Additionally, detection and/or localization of medical conditions for a patient associated with medical imaging data can also be improved. Accuracy and/or efficiency for classification and/or analysis of medical imaging data can also be improved. Moreover, effectiveness of a machine learning model for classification and/or analysis of medical imaging data can be improved, performance of one or more processors that execute a machine learning model for classification and/or analysis of medical imaging data can be improved, and/or efficiency of one or more processors that execute a machine learning model for classification and/or analysis of medical imaging data can be improved. Employing systems and/or techniques associated with the medical imaging stroke model disclosed herein also allows for dissemination of critical, neurologic findings when insights could be delayed with conventional methods of medical stroke care.

Referring initially to FIG. 1, there is illustrated an example system 100 that facilitates generating and/or employing a CT medical imaging stroke model, according to one or more embodiments of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In certain embodiments, the system 100 can be associated with a viewer system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include an medical imaging component 102 that can include a machine learning component 104 and a medical diagnosis component 106. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the medical imaging component 102) can include memory 110 for storing computer executable components and instructions. The system 100 (e.g., the medical imaging component 102) can further include a processor 108 to facilitate operation of the instructions (e.g., computer executable components and instructions) by the system 100 (e.g., the medical imaging component 102).

The medical imaging component 102 (e.g., the machine learning component 104) can receive computed tomography (CT) data 112 and diffusion-weighed imaging (DWI) data 114. The CT data 112 can include one or more CT images generated by one or more medical imaging devices. For example, the CT data 112 can include one or more CT images generated by one or more CT scanner devices. The one or more CT images of the CT data 112 can be related to an anatomical region (e.g., a brain anatomical region) of one or more patient bodies. In aspect, a CT image included in the CT data 112 can be a two-dimensional CT image or a three-dimensional CT image. In another aspect, the CT data 112 can be a series of X-ray images captured via a set of X-ray detectors (e.g., a set of X-ray detects associated with a medical imaging device). The CT data 112 can be received directly from one or more medical imaging devices. Alternatively, the CT data 112 can be stored in one or more databases that receives and/or stores the CT data 112 associated with the one or more medical imaging devices. In an embodiment, the CT data 112 can include one or more NCCT images generated without use of contrast medication by a patient. The DWI data 114 can include one or more one or more medical images generated by one or more medical imaging devices. For example, the DWI data 114 can include one or more DWI images generated by one or more MRI scanner devices. In an aspect, a medical image included in the DWI data 114 can be a DWI image that provides contrast based on a difference in a pattern of motion of water molecules with respect to an anatomical region (e.g., a brain anatomical region) of a patient body. For instance, a medical image included in the DWI data 114 can be a DWI image that provides a measurement of a pattern of motion of water molecules within a voxel of an anatomical region (e.g., a brain anatomical region). In another aspect, a medical image included in the DWI data 114 can be associated with darkness information for an anatomical region (e.g., a brain anatomical region). For instance, an amount of weighting for a parameter (e.g., a T1 parameter, a T2 parameter, etc.) employed to generate the DWI data 114 can provide an increased degree of darkness in the DWI data 114. In yet another aspect, a medical image included in the DWI data 114 can be a two-dimensional medical image or a three-dimensional medical image. For instance, the DWI data 114 can be electromagnetic radiation imagery captured via a set of sensors (e.g., a set of sensors associated with a medical imaging device). In certain embodiments, the DWI data 114 can be a series of electromagnetic radiation imagery captured via a set of sensors (e.g., a set of sensors associated with a medical imaging device) during an interval of time. The DWI data 114 can be received directly from one or more medical imaging devices. Alternatively, the DWI data 114 can be stored in one or more databases that receives and/or stores the DWI data 114 associated with the one or more medical imaging devices. A medical imaging device associated with the DWI data 114 can be, for example, an MRI device. In one example, the DWI data 114 can include one or more MRI DWI images. In certain embodiments, the CT data 112 and the DWI data 114 can both be acquired within a certain time frame (e.g., within 3 hours or less). For instance, the CT data 112 can be acquired by one or more CT scanner devices. Furthermore, within a certain time frame (e.g., within 3 hours or less) after the CT data 112 is acquired by the one or more CT scanner devices, the DWI data 114 can be acquired by one or more MRI scanner devices. As such, improved correlation of the CT data 112 and the DWI data 114 for generating training data for a convolutional neural network can be achieved.

The machine learning component 104 can employ a convolutional neural network to generate learned medical imaging stroke data regarding an anatomical region (e.g., a brain anatomical region) based on the CT data 112 and the DWI data 114. For instance, the machine learning component 104 can employ a convolutional neural network to generate learned medical imaging stroke data regarding an anatomical region (e.g., a brain anatomical region) based on the CT data 112 and one or more segmentation masks associated with the DWI data 114. The learned medical imaging stroke data can be output data generated by the convolutional neural network and/or information provided by the convolutional neural network. Furthermore, the one or more segmentation masks associated with the DWI data 114 can be related to a portion of an anatomical region (e.g., a brain anatomical region). For example, the one or more segmentation masks associated with the DWI data 114 can be related to a location of a stroke for an anatomical region (e.g., a brain anatomical region). The learned medical imaging stroke data can be, for example, deep learning data related to a stroke medical condition for an anatomical region (e.g., a brain anatomical region) associated with the CT data 112 and the DWI data 114. For instance, the learned medical imaging stroke data can classify and/or determine a location of a stroke for an anatomical region (e.g., a brain anatomical region) associated with the CT data 112 and the DWI data 114. In an embodiment, the machine learning component 104 can generate the learned medical imaging stroke data during a training phase for the convolutional neural network. For instance, the machine learning component 104 can employ the CT data 112 and the DWI data 114 as training data for the convolutional neural network to train the convolutional neural network to detect a stroke medical condition for an anatomical region (e.g., a brain anatomical region). The machine learning component 104 can analyze the CT data 112 and the DWI data 114 using deep learning and/or one or more machine learning techniques to generate the learned medical imaging stroke data. In an embodiment, the convolutional neural network employed by the machine learning component 104 can include a set of convolutional layers associated with upsampling and/or downsampling. Furthermore, in certain embodiments, the convolutional neural network can include a contracting path of convolutional layers and/or an expansive path of convolutional layers. In certain embodiments, the convolutional neural network can employ context data associated with previous inputs provided to the convolutional neural network and/or previous outputs provided by the convolutional neural network to analyze the CT data 112 and the DWI data 114. In a non-limiting embodiment, the convolutional neural network employed by the machine learning component 104 can be an adapted U-net model for analyzing the CT data 112 and the DWI data 114. For instance, the adapted U-net model can be a fully convolutional network that employs successive convolutional layers associated with downsampling followed by successive convolutional layers associated with upsampling. The adapted U-net model can also employ a segmentation loss function to modify one or more portions of the adapted U-net model. Additionally or alternatively, the adapted U-net model can employ a classification loss function to modify one or more portions of the adapted U-net model. However, it is to be appreciated that the convolutional neural network employed by the machine learning component 104 can be a different type of convolutional neural network. In an embodiment, the convolutional neural network employed by the machine learning component 104 can be a medical imaging stroke model that is trained to classify and/or locate a medical stroke condition (e.g., the ischemic stroke condition, the infarct, etc.) with respect to an anatomical region (e.g., a brain anatomical region) of a patient body.

In another embodiment, the machine learning component 104 can transform the DWI data 114 to match an orientation of the CT data 112. For instance, the machine learning component 104 can transform the one or more segmentations of the DWI data 114 to match an orientation of the CT data 112. For instance, the machine learning component 104 can spatially transform the DWI data 114 to match an orientation of the CT data 112. For instance, the machine learning component 104 can transform the one or more segmentations of the DWI data 114 to match an orientation of the CT data 112. In an aspect, the machine learning component 104 can rotate one or more DWI images of the DWI data 114 to match an orientation of one or more CT images of the CT data 112. In another aspect, the machine learning component 104 can rotate the DWI data 114 such that an anatomical region (e.g., a brain anatomical region) associated with the DWI data 114 matches an orientation of an anatomical region (e.g., a brain anatomical region) associated with the CT data 112. In another aspect, the machine learning component 104 can map spatial coordinates of one or more CT images of the CT data 112 and one or more DWI images of the DWI data 114 to facilitate matched orientation between the one or more CT images of the CT data 112 and the one or more DWI images of the DWI data 114. In yet another aspect, the machine learning component 104 can apply a registration (e.g., one or more transformation matrices) to the one or more segmentations of the DWI data 114 to facilitate matching an orientation of the DWI data 114 and the CT data 112. In yet another aspect, the machine learning component 104 can provide the CT data 112 and a transformed version of the DWI data 114 (e.g., a rotated version of the DWI data 114) to the convolutional neural network employed by the machine learning component 104. For instance, the machine learning component 104 can provide the CT data 112 and a transformed version of the one or more segmentation masks of the DWI data 114 (e.g., a rotation version of the one or more segmentation masks of the DWI data 114) to the convolutional neural network employed by the machine learning component 104.

In certain embodiments, the machine learning component 104 can extract information that is indicative of correlations, inferences and/or expressions from the CT data 112 and the DWI data 114 based on a convolutional neural network associated with a network of convolutional layers. Additionally or alternatively, the machine learning component 104 can generate the learned medical imaging stroke data based on the correlations, inferences and/or expressions. The machine learning component 104 can generate the learned medical imaging stroke data based on a network of convolutional layers. In an aspect, the machine learning component 104 can perform learning with respect to the CT data 112 and the DWI data 114 explicitly or implicitly using a network of convolutional layers. The machine learning component 104 can also employ an automatic classification system and/or an automatic classification process to facilitate analysis of the CT data 112 and the DWI data 114. For example, the machine learning component 104 can employ a probabilistic and/or statistical-based analysis (e.g., factoring into the analysis utilities and costs) to learn and/or generate inferences with respect to the CT data 112 and the DWI data 114. The machine learning component 104 can employ, for example, a support vector machine (SVM) classifier to learn and/or generate inferences for the CT data 112 and the DWI data 114. Additionally or alternatively, the machine learning component 104 can employ other classification techniques associated with Bayesian networks, decision trees and/or probabilistic classification models. Classifiers employed by the machine learning component 104 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, x=(x1, x2, x3, x4, xn), to a confidence that the input belongs to a class—that is, f(x)=confidence(class).

The medical diagnosis component 106 can employ information provided by the machine learning component 104 (e.g., the learned medical imaging stroke data) to classify and/or localize a medical condition associated with a CT image 115. The CT image 115 can be a CT image (e.g., a CT scan) generated by a medical imaging device. For example, the CT image 115 can be a CT image generated by a CT scanner device. In an embodiment, the CT image 115 can be a single CT image. In another embodiment, the CT image 115 can be a set of CT images acquired in a continuous order from across an anatomical region. Furthermore, the CT image 115 can be related to an anatomical region (e.g., a brain anatomical region) of a patient body scanned by the medical imaging device. For example, the CT image 115 can be related to an anatomical region (e.g., a brain anatomical region) of a patient body scanned by the CT scanner device. In aspect, the CT image 115 can be a two-dimensional CT image or a three-dimensional CT image. In another aspect, the CT image 115 can be represented as a series of X-ray images captured via a set of X-ray detectors (e.g., a set of X-ray detects associated with a medical imaging device) of the medical imaging device (e.g., the CT scanner device). The CT image 115 can be received directly from the medical imaging device (e.g., the CT scanner device). Alternatively, the CT image 115 can be stored in one or more databases that receives and/or stores the CT image 115 associated with the medical imaging device (e.g., the CT scanner device). In an embodiment, the CT image 115 can be a NCCT image generated without use of contrast medication by the patient associated with the anatomical region (e.g., the brain anatomical region).

In an embodiment, the medical diagnosis component 106 can determine a classification and an associated localization for a portion of the anatomical region (e.g., the brain anatomical region) based on the learned output data provided by a trained version of the convolutional neural network. In an aspect, the medical diagnosis component 106 can generate medical diagnosis data 116 based on the learned medical imaging stroke data associated with the CT data 112 and the DWI data 114. For instance, the medical diagnosis component 106 can employ a trained version of the convolutional neural network to generate the medical diagnosis data 116. Furthermore, in an embodiment, the medical diagnosis component 106 can detect, based on the learned medical imaging stroke data, presence or absence of a medical stroke condition associated with the anatomical region (e.g., the brain anatomical region) represented in the CT image 115. For instance, the medical diagnosis component 106 can employ a trained version of the convolutional neural network to detect presence or absence of a medical stroke condition associated with the anatomical region (e.g., the brain anatomical region) represented in the CT image 115. In an example, the medical diagnosis component 106 can detect, based on the learned medical imaging stroke data, presence or absence of an ischemic stroke condition associated with the anatomical region (e.g., the brain anatomical region) represented in the CT image 115. In certain embodiments, the medical diagnosis component 106 can detect, based on the learned medical imaging stroke data, presence or absence of an infarct associated with the anatomical region (e.g., the brain anatomical region) represented in the CT image 115. The infarct can be an area of the anatomical region (e.g., the brain anatomical region) that satisfies a defined criterion associated with a necrosis medical condition. For instance, the infarct can be an area of necrosis of the anatomical region (e.g., the brain anatomical region) resulting from lack of blood supply to the anatomical region (e.g., the brain anatomical region). Additionally, in another embodiment, the medical diagnosis component 106 can determine a size of the medical stroke condition based on the learned medical imaging stroke data. For example, the medical diagnosis component 106 can determine a size of the infarct based on the learned medical imaging stroke data. In an aspect, the medical diagnosis component 106 can determine an outline of the area of the anatomical region (e.g., the brain anatomical region) associated with the infarct.

In certain embodiments, the medical diagnosis component 106 can generate a contour mask associated with the medical stroke condition based on the learned medical imaging stroke data. For example, the medical diagnosis component 106 can generate a contour mask associated with the ischemic stroke condition based on the learned medical imaging stroke data. The contour mask can be, for example, an image that identifies a segmentation for the medical stroke condition. For instance, the contour mask can be an image that identifies a location of the area of the anatomical region (e.g., the brain anatomical region) associated with the infarct. The medical diagnosis data 116 can include information regarding presence or absence of the medical stroke condition (e.g., the ischemic stroke condition, the infarct, etc.), information regarding the size of the medical stroke condition (e.g., the ischemic stroke condition, the infarct, etc.), information regarding the contour mask associated with the medical stroke condition (e.g., the ischemic stroke condition, the infarct, etc.), and/or other information regarding the medical stroke condition (e.g., the ischemic stroke condition, the infarct, etc.). In an aspect, the medical diagnosis component 106 can determine a prediction for the medical stroke condition associated with the CT image 115. For example, the medical diagnosis component 106 can determine a probability score for the medical stroke condition associated with the CT image 115. In certain embodiments, the medical diagnosis component 106 can determine one or more confidence scores for the classification and/or the localization of the medical stroke condition. For example, a first portion of the anatomical region (e.g., the brain anatomical region) with a greatest likelihood of the medical stroke condition can be assigned a first confidence score, a second portion of the anatomical region (e.g., the brain anatomical region) with a lesser degree of likelihood of the medical stroke condition can be assigned a second confidence score, etc. A medical condition classified and/or localized by the medical diagnosis component 106 can additionally or alternatively include, for example, a tissue disease, a tumor, a cancer, or another type of medical condition associated with the anatomical region (e.g., the brain anatomical region). In certain embodiments, the medical diagnosis data 116 can be employed for a treatment decision associated with a patient body related to the CT image 115. For example, the medical diagnosis data 116 can be employed for a determining a particular endovascular therapy (e.g., determining an endovascular thrombectomy treatment) associated with a patient body related to the CT image 115. In another example, the medical diagnosis data 116 can be employed to determine if a medication treatment regime would be better suited to the specific features of learned machine learning model output provided by the convolutional neural network.

It is to be appreciated that technical features of the medical imaging component 102 (e.g., the machine learning component 104 and/or the medical diagnosis component 106) are highly technical in nature and not abstract ideas. Processing threads of the medical imaging component 102 (e.g., the machine learning component 104 and/or the medical diagnosis component 106) that process and/or analyze the CT data 112, DWI data 114 and/or the CT image 115, perform a machine learning process, generate the medical diagnosis data 116, etc. cannot be performed by a human (e.g., are greater than the capability of a single human mind). For example, the amount of the CT data 112, DWI data 114 and/or the CT image 115 processed, the speed of processing of the CT data 112, DWI data 114 and/or the CT image 115, and/or the data types of the CT data 112, DWI data 114 and/or the CT image 115 processed by the medical imaging component 102 (e.g., the machine learning component 104 and/or the medical diagnosis component 106) over a certain period of time can be respectively greater, faster and different than the amount, speed and data type that can be processed by a single human mind over the same period of time. Furthermore, the CT data 112, DWI data 114 and/or the CT image 115 processed by the medical imaging component 102 (e.g., the machine learning component 104 and/or the medical diagnosis component 106) can be one or more medical images generated by sensors of a medical imaging device. Moreover, the medical imaging component 102 (e.g., the machine learning component 104 and/or the medical diagnosis component 106) can be fully operational towards performing one or more other functions (e.g., fully powered on, fully executed, etc.) while also analyzing the CT data 112, DWI data 114 and/or the CT image 115.

Figure 2:
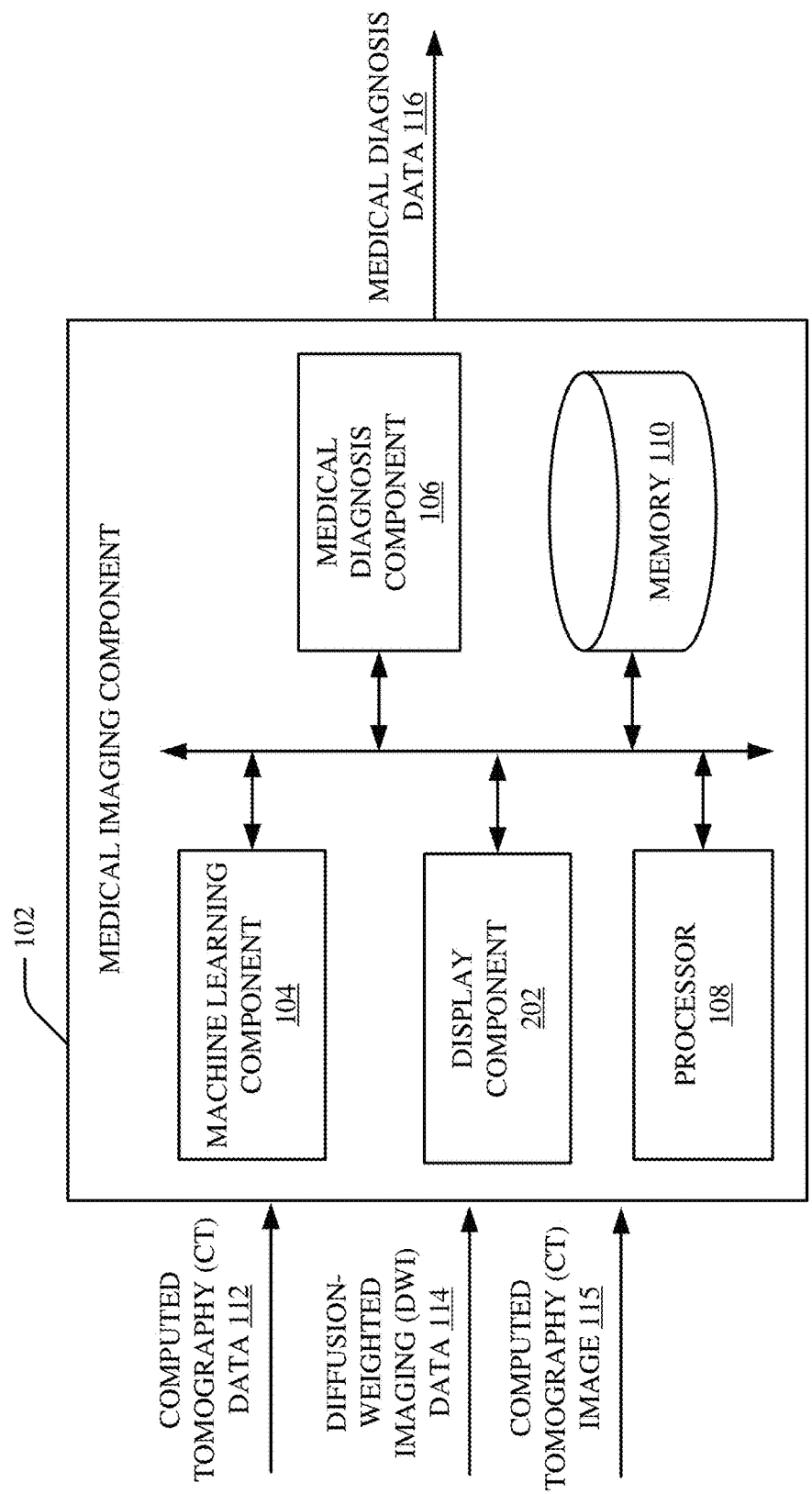
FIG. 2 illustrates a high-level block diagram of another example medical imaging component, in accordance with one or more embodiments described herein.

FIG. 2 illustrates an example, non-limiting system 200 in accordance with one or more embodiments described herein. Repetitive description of like elements employed in other embodiments described herein is omitted for sake of brevity. The system 200 includes the medical imaging component 102. In the embodiment shown in FIG. 2, the medical imaging component 102 can include the machine learning component 104, the medical diagnosis component 106, a display component 202, the processor 108 and/or the memory 110. The display component 202 can generate display data associated with the medical diagnosis data 116. Furthermore, the display component 202 can provide the display data to a user device in a human-interpretable format. In an embodiment, the display component 202 can generate display data associated with the presence or the absence of the medical stroke condition (e.g., the ischemic stroke condition, the infarct, etc.) in a human-interpretable format. Additionally or alternatively, the display component 202 can generate display data associated with the size of the medical stroke condition (e.g., the ischemic stroke condition, the infarct, etc.) in a human-interpretable format. Additionally or alternatively, the display component 202 can generate display data associated with the contour mask associated with the medical stroke condition (e.g., the ischemic stroke condition, the infarct, etc.) in a human-interpretable format. Additionally or alternatively, the display component 202 can generate display data associated with other information regarding the medical stroke condition (e.g., the ischemic stroke condition, the infarct, etc.) in a human-interpretable format. In certain embodiments, the display component 202 can generate a multi-dimensional visualization associated with the medical diagnosis data 116. For example, the display component 202 can generate a multi-dimensional visualization associated with the presence or the absence of the medical stroke condition (e.g., the ischemic stroke condition, the infarct, etc.). Additionally or alternatively, the display component 202 can generate a multi-dimensional visualization associated with the size of the medical stroke condition (e.g., the ischemic stroke condition, the infarct, etc.). Additionally or alternatively, the display component 202 can generate a multi-dimensional visualization associated with the contour mask associated with the medical stroke condition (e.g., the ischemic stroke condition, the infarct, etc.). Additionally or alternatively, the display component 202 can generate a multi-dimensional visualization associated with the CT image 115. Additionally or alternatively, the display component 202 can generate a multi-dimensional visualization associated with other information regarding the medical stroke condition (e.g., the ischemic stroke condition, the infarct, etc.). The multi-dimensional visualization can be a graphical representation of the CT image 115 and/or other medical imaging data that shows a classification and/or a location of the medical stroke condition (e.g., the ischemic stroke condition, the infarct, etc.) with respect to a patient body.

The display component 202 can also generate, in certain embodiments, a graphical user interface of the multi-dimensional visualization of the medical diagnosis data 116. For example, the display component 202 can render a 2D visualization of the portion of the anatomical region (e.g., the brain anatomical region) on a graphical user interface associated with a display of a user device such as, but not limited to, a computing device, a computer, a desktop computer, a laptop computer, a monitor device, a smart device, a smart phone, a mobile device, a handheld device, a tablet, a portable computing device, a virtual reality device, a wearable device, or another type of user device associated with a display. In an aspect, the multi-dimensional visualization can include the medical diagnosis data 116. In certain embodiments, the medical diagnosis data 116 associated with the multi-dimensional visualization can be indicative of a visual representation of the classification and/or the localization for the portion of the anatomical region (e.g., the brain anatomical region). In certain embodiments, the medical diagnosis data 116 can be rendered on the CT image 115 and/or a 3D model associated with the CT image 115 as one or more dynamic visual elements. In an aspect, the display component 202 can alter visual characteristics (e.g., color, size, hues, shading, etc.) of at least a portion of the medical diagnosis data 116 associated with the multi-dimensional visualization based on the classification and/or the localization for the portion of the anatomical region (e.g., the brain anatomical region). For example, the classification and/or the localization for the medical stroke condition (e.g., the ischemic stroke condition, the infarct, etc.) can be presented as different visual characteristics (e.g., colors, sizes, hues or shades, etc.), based on a result of deep learning and/or medical imaging diagnosis by the machine learning component 104 and/or the medical diagnosis component 106. As such, a user can view, analyze and/or interact with the medical diagnosis data 116 associated with the multi-dimensional visualization. In certain embodiments, the display component 202 can query and/or display clinical data, demographic data, and/or historical data resident in an electronic health record system database in context with the learned medical imaging stroke data and/or the medical diagnosis data 116. For example, in certain embodiments, the display component 202 can query and/or display clinical data, demographic data, and/or historical data resident in an electronic health record system database in context with diagnostic output generated by the convolutional neural network (e.g., the machine learning model). In certain embodiments, the display component 202 can generate and/or transmit one or more alerts based on the medical diagnosis data 116. An alert generated and/or transmitted by the display component 202, in certain embodiments, can be a message and/or a notification to provide machine-to-person communication related to the medical diagnosis data 116. Furthermore, an alert generated and/or transmitted by the display component 202 can include textual data, audio data, video data, graphic data, graphical user interface data, and/or other data related to the medical diagnosis data 116.

Figure 3:
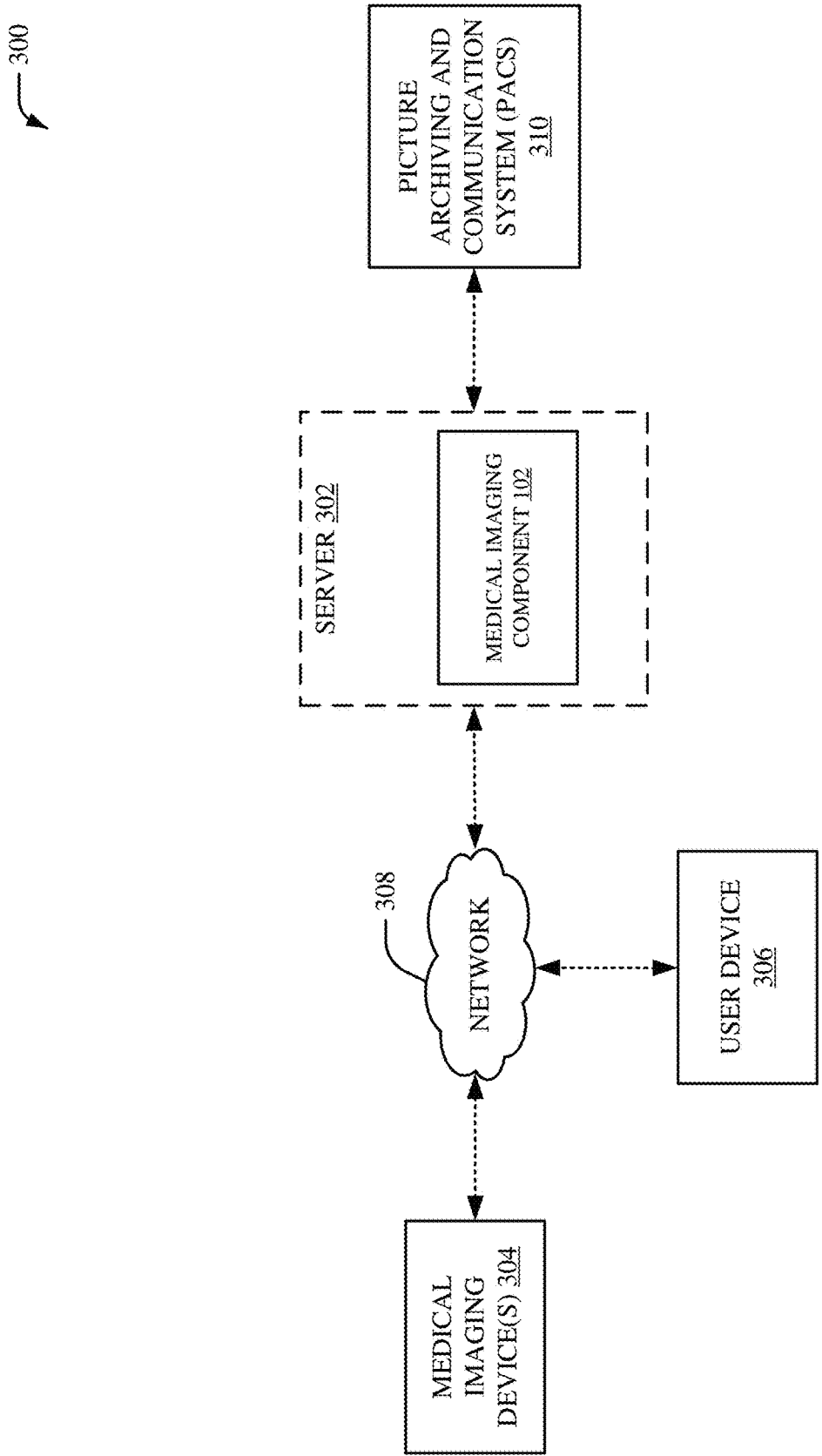
FIG. 3 illustrates an example system that facilitates generating and/or employing a computed tomography medical imaging stroke model, in accordance with one or more embodiments described herein.

FIG. 3 illustrates an example, non-limiting system 300 in accordance with one or more embodiments described herein. Repetitive description of like elements employed in other embodiments described herein is omitted for sake of brevity. The system 300 can be, for example, a network environment (e.g., a network computing environment, a healthcare network environment, etc.) to facilitate generating and/or employing a medical imaging stroke model. The system 300 includes a server 302, one or more medical imaging devices 304 and/or a user device 306. The server 302 can include the medical imaging component 102. The medical imaging component 102 can include the machine learning component 104, the medical diagnosis component 106, the display component 202, the processor 108 and/or the memory 110.

In certain embodiments, the medical imaging component 102 can be alternatively included in the medical imaging device 304. In certain embodiments, a portion of the medical imaging component 102 can be included in the server 302 and another portion of the medical imaging component 102 can be included in the one or more medical imaging devices 304. The one or more medical imaging devices 304 can generate, capture and/or process at least a portion of the CT data 112, the DWI data 114 and/or the CT image 115. The one or more medical imaging devices 304 can include one or more CT scanner devices, one or more MRI scanner devices, one or more computerized axial tomography (CAT) devices, one or more X-ray devices, one or more positron emission tomography (PET) devices, one or more ultrasound devices, and/or one or more other types of medical imaging devices. In an embodiment, one or more CT scanner devices from the one or more medical imaging devices 304 can generate the CT data 112. For example, a set of X-ray detectors of one or more CT scanner devices from the one or more medical imaging devices 304 can facilitate generating, capturing and/or processing at least a portion of the CT data 112. Additionally, one or more MRI scanner devices from the one or more medical imaging devices 304 can generate the DWI data 114. For example, a set of sensors of one or more MRI scanner devices from the one or more medical imaging devices 304 can facilitate generating, capturing and/or processing at least a portion of the DWI data 114. In certain embodiments, the DWI data 114 can be employed to update and/or create a new version of a trained machine learning model. In another embodiment, a CT scanner device from the one or more medical imaging devices 304 can generate the CT image 115. For example, a set of X-ray detectors of a CT scanner device from the one or more medical imaging devices 304 can facilitate generating, capturing and/or processing at least a portion of the CT image 115. In an implementation, a CT scanner device from the one or more medical imaging devices 304 that generates the CT image 115 can be different than one or more CT scanner devices from the one or more medical imaging devices 304 that generate the CT data 112. In an alternate implementation, a CT scanner device from the one or more medical imaging devices 304 that generates the CT image 115 can correspond to a CT scanner device from the one or more medical imaging devices 304 that generates the CT data 112.

The user device 306 can be an electronic device associated with a display. For example, the user device 306 can be a screen, a monitor, a projector wall, a computing device, an electronic device, a desktop computer, a laptop computer, a smart device, a smart phone, a mobile device, a handheld device, a tablet device, a virtual reality device, a portable computing device, a wearable device, or another display device associated with a display configured to present information associated with the medical diagnosis data 116 in a human-interpretable format. In an embodiment, the user device 306 can include a graphical user interface to facilitate display of information associated with the medical diagnosis data 116 in a human-interpretable format. In certain embodiments, the user device 306 can receive one or more alerts from the medical imaging component 102 (e.g., the display component 202) of the server 302. Additionally or alternatively, in certain embodiments, the one or more medical imaging devices 304 can receive one or more alerts from the medical imaging component 102 (e.g., the display component 202) of the server 302. In an embodiment, the server 302 can be in communication with the one or more medical imaging devices 304 and/or the user device 306 via a network 308. The network 308 can be a communication network, a wireless network, a wired network, an internet protocol (IP) network, a voice over IP network, an internet telephony network, a mobile telecommunications network or another type of network. In certain embodiments, visual characteristics (e.g., color, size, hues, shading, etc.) of a visual element associated with the medical diagnosis data 116 and/or presented via the user device 306 can be altered based on a value of the medical diagnosis data 116. In certain embodiments, a user can view, analyze and/or interact with the CT data 112, the DWI data 114, the CT image 115 and/or the medical diagnosis data 116 via the user device 306. In certain embodiments, the user device 306 can be two or more user devices at two or more locations. As such, in certain embodiments, the system 300 can allow interaction with multiple users across a geographic region. Furthermore, the system 300 can additionally or alternatively allow one or more notifications and/or one or more alerts to be provided to the two or more user devices at two or more locations. In an embodiment, the medical imaging component 102 can be in communication with picture archiving and communication system (PACS) 310. The PACS 310 can store and/or manage the CT data 112 and/or DWI data 114, for example. For example, the PACS 310 can be an imaging storage and transfer system that stores and/or manages the CT data 112 and/or DWI data 114. Furthermore, in certain embodiments, the PACS 310 can provide the CT data 112 and/or DWI data 114 to the medical imaging component 102 to facilitate training of the convolutional neural network employed by the medical imaging component 102. In certain embodiments, the server 302 that includes the medical imaging component 102 can be a remote hosted set of servers (e.g., a cloud computing network). Furthermore, in certain embodiments, the medical imaging component 102 can be managed by a set of logic and/or software that provide access to machine learning output for clinical care team members associated with user devices at various locations. Medical image data and/or machine learning outputs can accessible to the clinical care team members. Updates and/or interactions with machine learning outputs can also be managed through user interactions on a display unit associate with a user device. A type of interactions could include, for example, concurring with machine learning outputs, disagreeing with machine learning outputs, providing expert interpretation for future machine learning, concurring with clinical data, disagreeing with clinical data, providing expert interpretation for clinical data, and/or another type of interaction.

Figure 4:
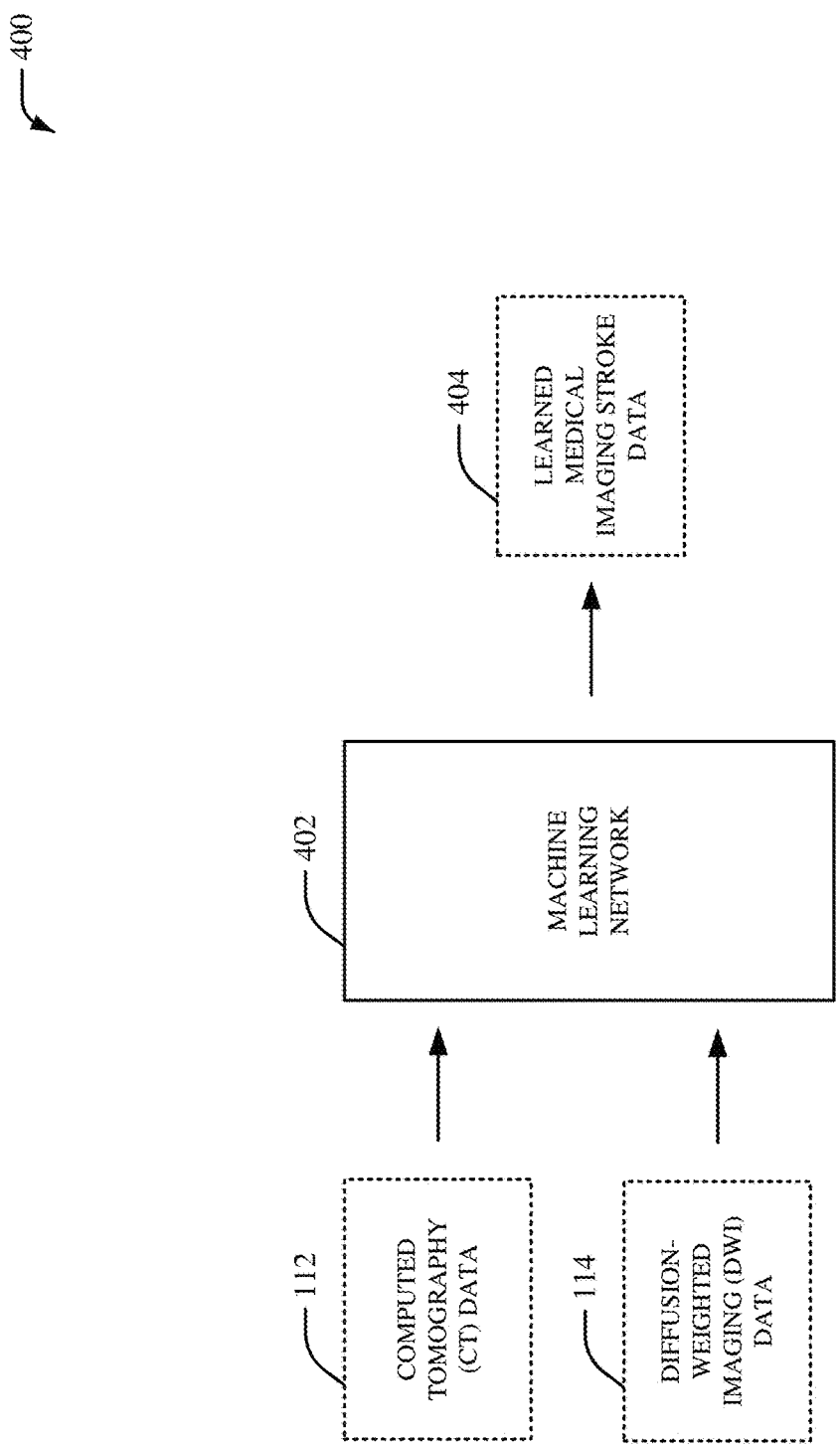
FIG. 4 illustrates another example system that facilitates generating and/or employing a computed tomography medical imaging stroke model, in accordance with one or more embodiments described herein.

FIG. 4 illustrates an example, non-limiting system 400 in accordance with one or more embodiments described herein. Repetitive description of like elements employed in other embodiments described herein is omitted for sake of brevity. The system 400 includes a machine learning network 402. In an embodiment, the system 400 can be associated with a training phase for the machine learning network 402. In an aspect, the machine learning network 402 can generate learned medical imaging stroke data 404 based on the CT data 112 and the DWI data 114. For instance, the CT data 112 and the DWI data 114 can be provided as training data for the machine learning network 402. The machine learning network 402 can be, for example, a machine learning network employed by the machine learning component 104 to generate the learned medical imaging stroke data 404. The learned medical imaging stroke data 404 can be, for example, deep learning data related to a stroke medical condition for the anatomical region (e.g., the brain anatomical region) associated with the CT data 112 and the DWI data 114. For example, the learned medical imaging stroke data 404 can, for example, classify and/or determine a location of a stroke for the anatomical region (e.g., the brain anatomical region) associated with the CT data 112 and the DWI data 114. In an aspect, the learned medical imaging stroke data 404 can include one or more segmentations related to an area of the stroke medical condition for the anatomical region (e.g., the brain anatomical region) associated with the CT data 112 and the DWI data 114. The machine learning network 402 can analyze the CT data 112 and the DWI data 114 using deep learning and/or one or more machine learning techniques to generate the learned medical imaging stroke data 404. In an embodiment, the machine learning network 402 can be a convolutional neural network. For instance, the machine learning network 402 can include a set of convolutional layers associated with upsampling and/or downsampling. Furthermore, in certain embodiments, the machine learning network 402 can include a contracting path of convolutional layers and/or an expansive path of convolutional layers. In certain embodiments, the machine learning network 402 can employ context data associated with previous inputs provided to the convolutional neural network and/or previous outputs provided by the convolutional neural network to analyze the CT data 112 and the DWI data 114. In a non-limiting embodiment, the machine learning network 402 can be an adapted U-net model for analyzing the CT data 112 and the DWI data 114. For instance, the machine learning network 402 can be a fully convolutional network that employs successive convolutional layers associated with downsampling followed by successive convolutional layers associated with upsampling. The machine learning network 402 can also employ a segmentation loss function to modify one or more portions of the adapted U-net model. Additionally or alternatively, the machine learning network 402 can employ a classification loss function to modify one or more portions of the adapted U-net model by the machine learning network 402. In an embodiment, the machine learning network 402 can be a medical imaging stroke model that is trained to classify and/or locate a medical stroke condition (e.g., the ischemic stroke condition, the infarct, etc.) with respect to an anatomical region (e.g., a brain anatomical region) of a patient body. However, it is to be appreciated that, in certain embodiments, the machine learning network 402 can be a different type of machine learning network and/or a different type of machine learning model that generates the learned medical imaging stroke data 404 based on analysis of the CT data 112 and the DWI data 114.

Figure 5:
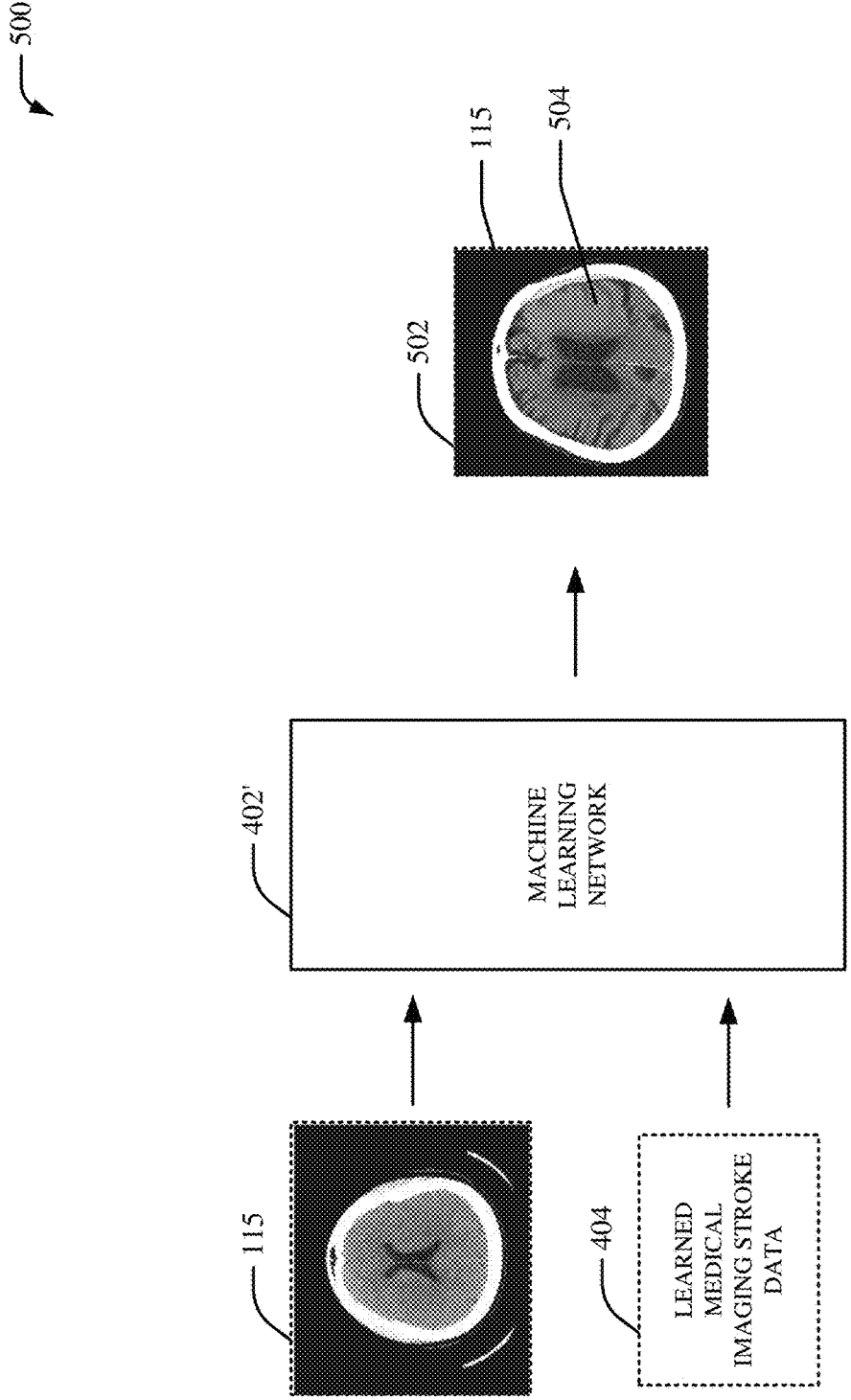
FIG. 5 illustrates yet another example system that facilitates generating and/or employing a computed tomography medical imaging stroke model, in accordance with one or more embodiments described herein.

FIG. 5 illustrates an example, non-limiting system 500 in accordance with one or more embodiments described herein. Repetitive description of like elements employed in other embodiments described herein is omitted for sake of brevity. The system 500 includes a machine learning network 402'. For instance, in an embodiment, the machine learning network 402' included in the system 500 can be a trained version of the machine learning network 402 included in the system 400. The machine learning network 402' can be a machine learning network that was previously trained, for example, based on the CT data 112 and the DW data 114. Additionally, the machine learning network 402' can be, for example, a machine learning network employed by the medical diagnosis component 106 to generate the medical diagnosis data 116. For example, the medical diagnosis component 106 can, for example, classify and/or determine a location of a stroke for an anatomical region (e.g., the brain anatomical region) associated with the CT image 115. The machine learning network 402' can analyze the CT image 115 using deep learning and/or one or more machine learning techniques associated with the learned medical imaging stroke data 404 to generate a segmented CT image 502.

In an embodiment, the machine learning network 402' can be a convolutional neural network. For instance, the machine learning network 402' can include a set of convolutional layers associated with upsampling and/or downsampling. Furthermore, in certain embodiments, the machine learning network 402' can include a contracting path of convolutional layers and/or an expansive path of convolutional layers. In certain embodiments, the machine learning network 402' can employ context data associated with previous inputs provided to the convolutional neural network and/or previous outputs provided by the convolutional neural network to analyze the CT image 115. In a non-limiting embodiment, the machine learning network 402' can be an adapted U-net model for analyzing the CT image 115. For instance, the machine learning network 402' can be a fully convolutional network that employs successive convolutional layers associated with downsampling followed by successive convolutional layers associated with upsampling. The machine learning network 402' can also employ a segmentation loss function to modify one or more portions of the adapted U-net model. Additionally or alternatively, the machine learning network 402' can employ a classification loss function to modify one or more portions of the adapted U-net model by the machine learning network 402'. In an embodiment, the machine learning network 402' can be a trained medical imaging stroke model that is previously trained to classify and/or locate a medical stroke condition (e.g., the ischemic stroke condition, the infarct, etc.) with respect to an anatomical region (e.g., a brain anatomical region) of a patient body. However, it is to be appreciated that, in certain embodiments, the machine learning network 402' can be a different type of machine learning network and/or a different type of machine learning model that generates the segmented CT image 502 based on analysis of the CT image 115 and/or by employing the learned medical imaging stroke data 404. In certain embodiments, other data can additionally be employed by the machine learning network 402'. For example, in certain embodiments, information related to a state of a patient associated with the CT image 502 can be provided to the machine learning network 402'. The information related to a state of a patient can include, for example, clinical symptomology data, heart-rate data, blood pressure data and/or other patient data. In certain embodiments, the machine learning network 402' can employ the information related to a state of a patient to refine decision making steps associated with the machine learning network 402'.

The segmented CT image 502 can be, for example, a segmented CT image where a segmentation mask 504 generated by the machine learning network 402' is overlaid onto the CT image 115. For example, the segmentation mask 504 can correspond to an area of an anatomical region (e.g., a brain anatomical region) associated with a medical stroke condition (e.g., an ischemic stroke condition, an infarct, etc.). The segmented CT image 502 can include, for example, one or more segmentations related to an area of the stroke medical condition for the anatomical region (e.g., the brain anatomical region) associated with the CT image 115. In one example, the segmentation mask 504 can be a contour mask related to a segmentation that corresponds to an area of an anatomical region (e.g., a brain anatomical region) associated with a medical stroke condition (e.g., an ischemic stroke condition, an infarct, etc.). In an embodiment, the segmentation mask 504 and/or the segmented CT image 502 can be included in the medical diagnosis data 116. The machine learning network 402' can be, for example, a machine learning network employed by the medical diagnosis component 106 to generate the segmented CT image 502.

Figure 6:
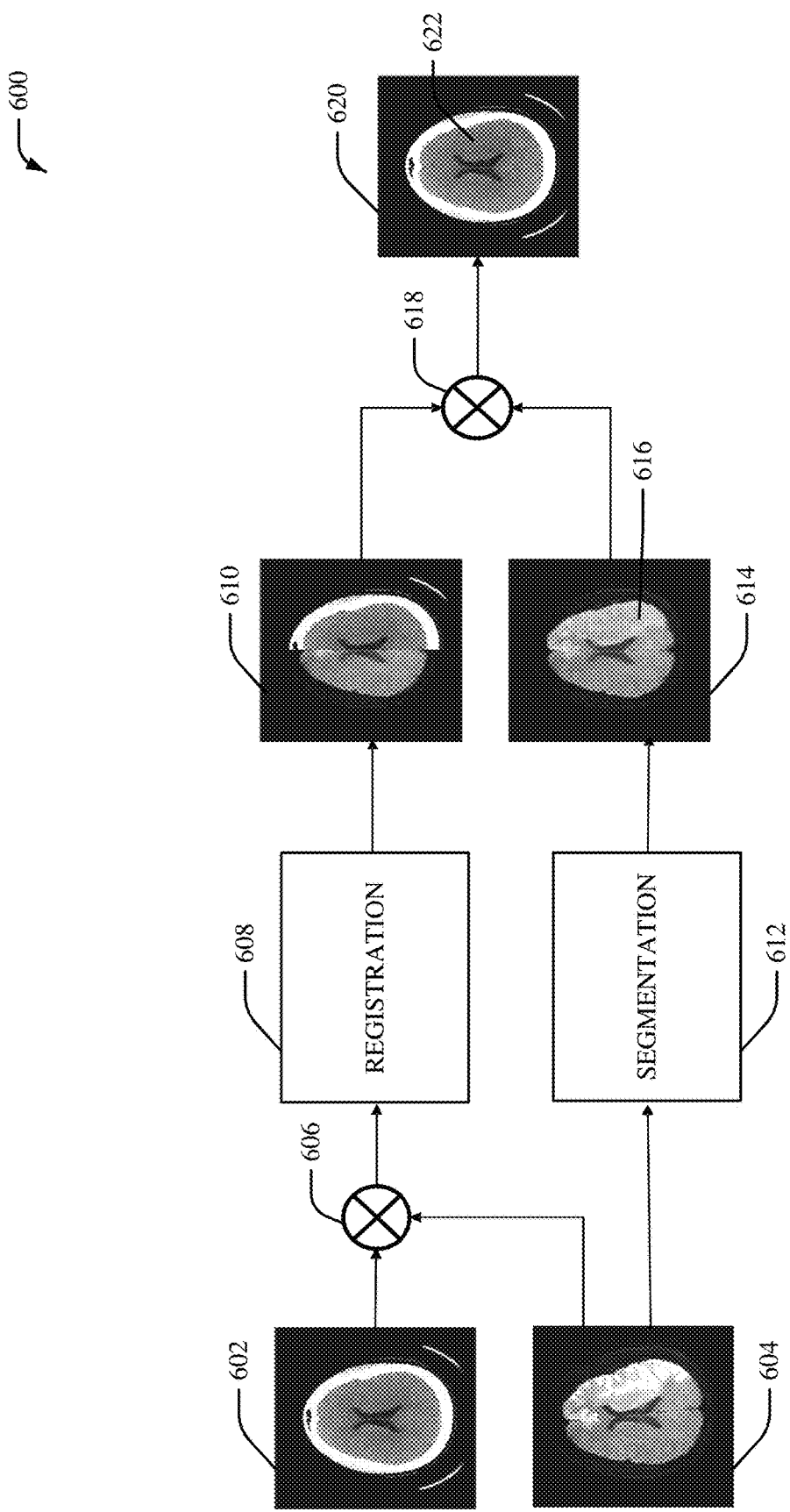
FIG. 6 illustrates yet another example system that facilitates generating and/or employing a computed tomography medical imaging stroke model, in accordance with one or more embodiments described herein.

FIG. 6 illustrates an example, non-limiting system 600 in accordance with one or more embodiments described herein. Repetitive description of like elements employed in other embodiments described herein is omitted for sake of brevity. The system 600 includes a CT image 602 and a DWI MRI image 604. In an embodiment, the system 600 can be associated with a training phase for a convolutional neural network (e.g., the machine learning network 402) employed by the medical imaging component 102. The CT image 602 can be, for example, a CT image included in the CT data 112. The DWI MRI image 604 can be, for example, a DWI MRI image included in the DWI data 114. In an embodiment, the CT image 602 can be generated by a CT scanner device. Furthermore, the CT image 602 can be related to an anatomical region (e.g., a brain anatomical region) of a patient body that is scanned by the CT scanner device. The DWI MRI image 604 can be generated by an MRI scanner device, in an embodiment. In an embodiment, a process 606 (e.g., a mapping process) can be performed (e.g., by the machine learning component 104) to map spatial coordinates of the CT image 602 and the DWI MRI image 604. In another embodiment, registration 608 (e.g., a registration process) can be performed (e.g., by the machine learning component 104) to spatially transform the DWI MRI image 604 and the CT image into a DWI CT image 610. In an aspect, the DWI CT image 610 can be a translated version of the DWI MRI image 604 with respect to an orientation of the CT image 602. For instance, an orientation of the DWI MRI image 604 can be translated to match an orientation of the CT image 602. As such, in an embodiment, the DWI CT image 610 can include the CT image 602 and a translated version of the DWI MRI image 604. In another embodiment, segmentation 612 (e.g., a segmentation process) can be performed (e.g., by the machine learning component 104) to identify area of an anatomical region (e.g., a brain anatomical region) of the DWI MRI image 604 associated with a medical stroke condition (e.g., an ischemic stroke condition, an infarct, etc.). For example, one or more segmentation masks that that correspond to an area of an anatomical region (e.g., a brain anatomical region) associated with a medical stroke condition (e.g., an ischemic stroke condition, an infarct, etc.) in the DWI MRI image 604 can be determined via the segmentation 612. In an aspect, a segmented DWI MRI image 614 that corresponds to a segmented version of the DWI MRI 604 can be generated by the segmentation 612. For instance, the segmented DWI MRI image 614 can include a segmentation mask 616 (e.g., a contour mask) that corresponds to area of an anatomical region (e.g., a brain anatomical region) of the DWI MRI image 604 associated with a medical stroke condition (e.g., an ischemic stroke condition, an infarct, etc.). In yet another embodiment, a process 618 (e.g., a multi-dimensional visualization process) can be performed to apply the segmented DWI MRI image 614 to the DWI CT image 610. For instance, the registration (e.g., the transformation matrices) can be applied to the segmentation mask 616. Furthermore, the segmentation mask 616 can be overlaid onto the DWI CT image 610. For instance, in an embodiment, the segmentation mask 616 can be overlaid onto the CT image 602 to generate a segmented CT image 620. For instance, the segmented CT image 620 can include a segmentation mask 622 (e.g., a contour mask) that corresponds to area of an anatomical region (e.g., a brain anatomical region) of the CT image 602 associated with a medical stroke condition (e.g., an ischemic stroke condition, an infarct, etc.).

Figure 7:
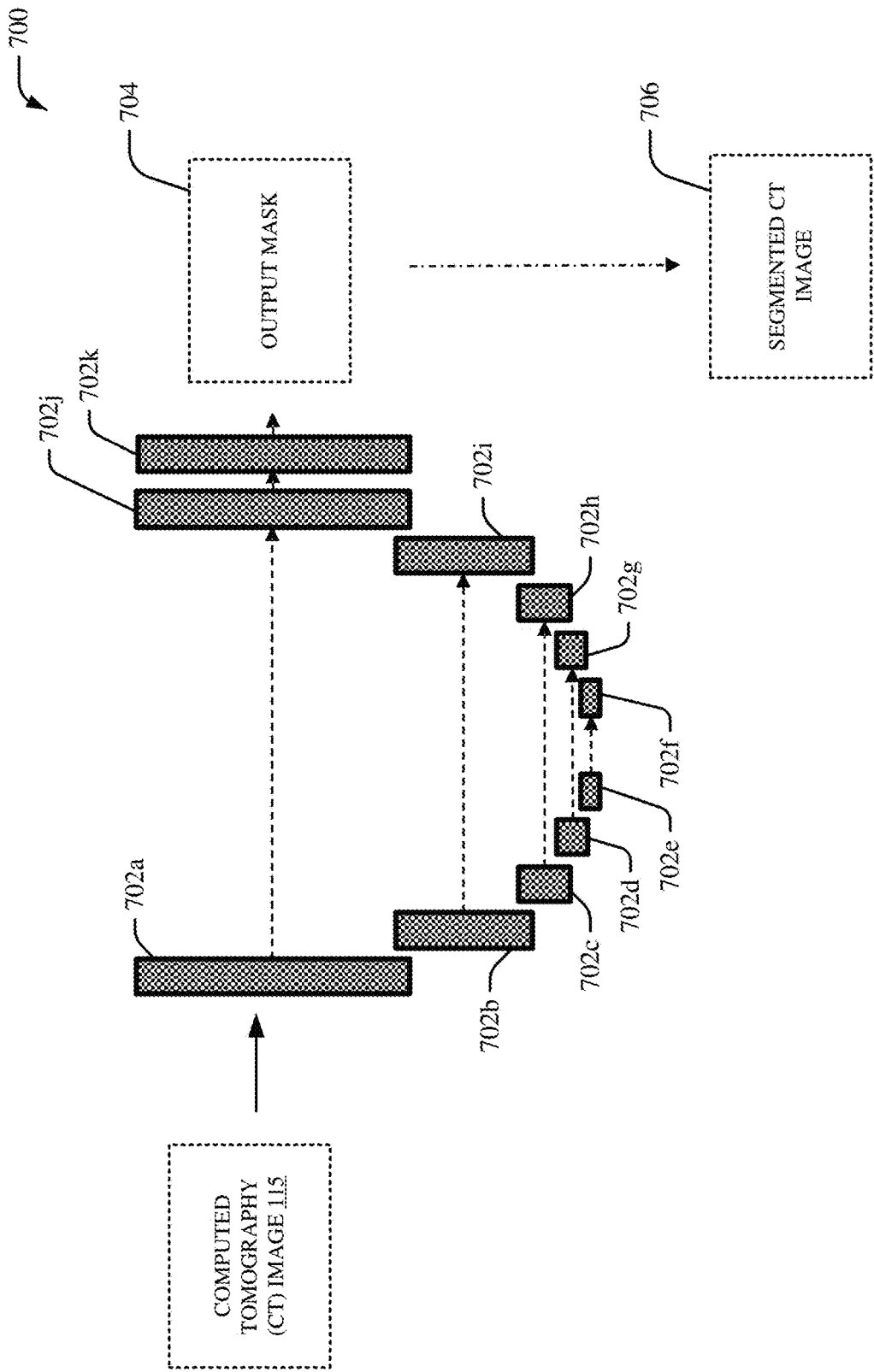
FIG. 7 illustrates yet another example system that facilitates generating and/or employing a computed tomography medical imaging stroke model, in accordance with one or more embodiments described herein.

FIG. 7 illustrates an example, non-limiting system 700 in accordance with one or more embodiments described herein. Repetitive description of like elements employed in other embodiments described herein is omitted for sake of brevity. The system 700 includes a set of convolutional layers 702a-k that generates an output mask 704 based on the CT image 115. The output mask 704 can be, for example, a segmentation mask (e.g., a contour mask) related to a segmentation that corresponds to an area of an anatomical region (e.g., a brain anatomical region) associated with a medical stroke condition (e.g., an ischemic stroke condition, an infarct, etc.). The set of convolutional layers 702a-k can be, for example, a convolutional neural network (e.g., the machine learning network 402') employed by the machine learning component 104 to generate the output mask 704. The output mask 704 can be related to a stroke medical condition for the anatomical region (e.g., the brain anatomical region) associated with the CT image 115. For example, the output mask 704 can provide a location of a stroke for the anatomical region (e.g., the brain anatomical region) associated with the CT image 115. In an aspect, the output mask 704 can include one or more segmentations related to an area of the stroke medical condition for the anatomical region (e.g., the brain anatomical region) associated with the CT image 115. In an aspect, the output mask 704 can be a contour mask related to a segmentation that corresponds to an area of an anatomical region (e.g., a brain anatomical region) associated with a medical stroke condition (e.g., an ischemic stroke condition, an infarct, etc.). The set of convolutional layers 702a-k can analyze the CT image 115 using deep learning and/or one or more machine learning techniques to generate the output mask 704. In an embodiment, the set of convolutional layers 702a-k can include a first set of convolutional layers 702a-e associated with downsampling and a second set of convolutional layers 702f-j associated with upsampling. For instance, the set of convolutional layers 702a-k can be a contracting path of convolutional layers and the second set of convolutional layers 702f-j can be an expansive path of convolutional layers. In another aspect, a convolutional layer 702k can include a size that corresponds to the convolutional layer 702j to, for example, facilitate batch normalization and/or a rectified linear activation function. In a non-limiting embodiment, the set of convolutional layers 702a-k can be an adapted U-net model for analyzing the CT image 115. For instance, the set of convolutional layers 702a-k can be a fully convolutional network that employs successive convolutional layers associated with downsampling followed by successive convolutional layers associated with upsampling. In an embodiment, the set of convolutional layers 702a-k can be a medical imaging stroke model that is trained to classify and/or locate a medical stroke condition (e.g., the ischemic stroke condition, the infarct, etc.) with respect to an anatomical region (e.g., a brain anatomical region) of a patient body. In an embodiment, the output mask 704 generated by the set of convolutional layers 702a-k can be employed to generate a segmented CT image 706. The segmented CT image 706 can be, for example, a segmented CT image where the output mask 704 generated by the set of convolutional layers 702a-k is overlaid on the CT image 115. The segmented CT image 706 can include, for example, one or more segmentations related to an area of the stroke medical condition for the anatomical region (e.g., the brain anatomical region) associated with the CT image 115. In an embodiment, the output mask 704 and/or the segmented CT image 706 can be included in the medical diagnosis data 116.

Figure 8:
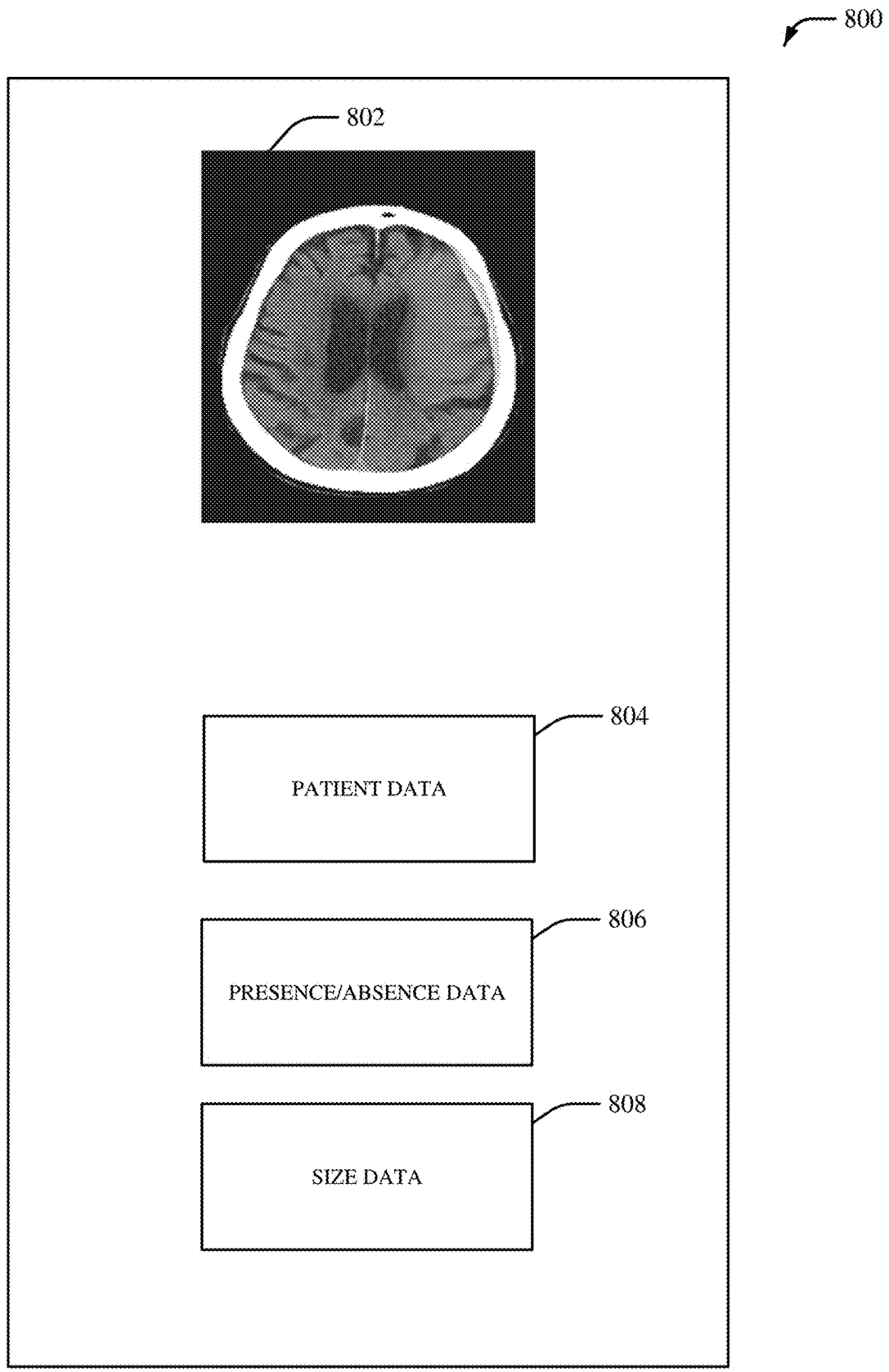
FIG. 8 illustrates an example user interface, in accordance with one or more embodiments described herein.

FIG. 8 illustrates an example user interface 800, in accordance with various aspects and implementations described herein. Repetitive description of like elements employed in other embodiments described herein is omitted for sake of brevity. The user interface 800 can be a display environment for medical imaging data and/or medical diagnosis data (e.g., the medical diagnosis data 116). Furthermore, in an embodiment, the user interface 800 can be a graphical user interface presented on a display. In certain embodiments, the user interface 800 can be displayed via a user device (e.g., the user device 306). The user interface 800 can include medical imaging data 802. In one embodiment, the medical imaging data 802 can be a multi-dimensional visualization associated with the presence or the absence of a medical stroke condition (e.g., an ischemic stroke condition, an infarct, etc.) determined by the medical imaging component 102. For example, the medical imaging data 802 can be displayed as a segmented CT image associated with an anatomical region (e.g., a brain anatomical region) of a patient where a contour mask associated with a segmentation for a medical stroke condition e.g., an ischemic stroke condition, an infarct, etc.) is overlaid on a CT image (e.g., the CT image 115). The user interface 800 can also include patient information 804, in certain embodiments. The patient information 804 can include information regarding a patient (e.g., a patient body) associated with the medical imaging data 802. For example, the patient information 804 can include patient identification data, patient medical record data, patient medical chart data, patient medical history data, patient medical monitoring data, and/or other patient data. In an embodiment, the patient information 804 can include information regarding a patient (e.g., a patient body) associated with the CT image 115.

The user interface 800 can additionally or alternatively include presence/absence data 806. The presence/absence data 806 can include an indication as to whether a medical stroke condition (e.g., an ischemic stroke condition, an infarct, etc.) is present or absent in the medical imaging data 802. For instance, the presence/absence data 806 can include an indication as to whether a medical stroke condition (e.g., an ischemic stroke condition, an infarct, etc.) is present or absent in the CT image 115. In certain embodiments, the presence/absence data 806 can be determined by the medical imaging component 102 (e.g., the machine learning component 104 and/or the medical diagnosis component 106). For example, the presence/absence data 806 can be included in the medical diagnosis data 116. In an embodiment, the presence/absence data 806 can be presented as textual data and/or visual data via the user interface 800. The user interface 800 can additionally or alternatively include size data 808. The size data 808 can include an indication as to a size of a medical stroke condition (e.g., an ischemic stroke condition, an infarct, etc.) associated with the medical imaging data 802. For instance, the size data 808 can include an indication as to a size of a medical stroke condition (e.g., an ischemic stroke condition, an infarct, etc.) with respect to a patient body related to the CT image 115. In certain embodiments, the size data 808 can be determined by the medical imaging component 102 (e.g., the machine learning component 104 and/or the medical diagnosis component 106). For example, the size data 808 can be included in the medical diagnosis data 116. In an embodiment, the size data 808 can be presented as textual data and/or visual data via the user interface 800.

Figure 9:
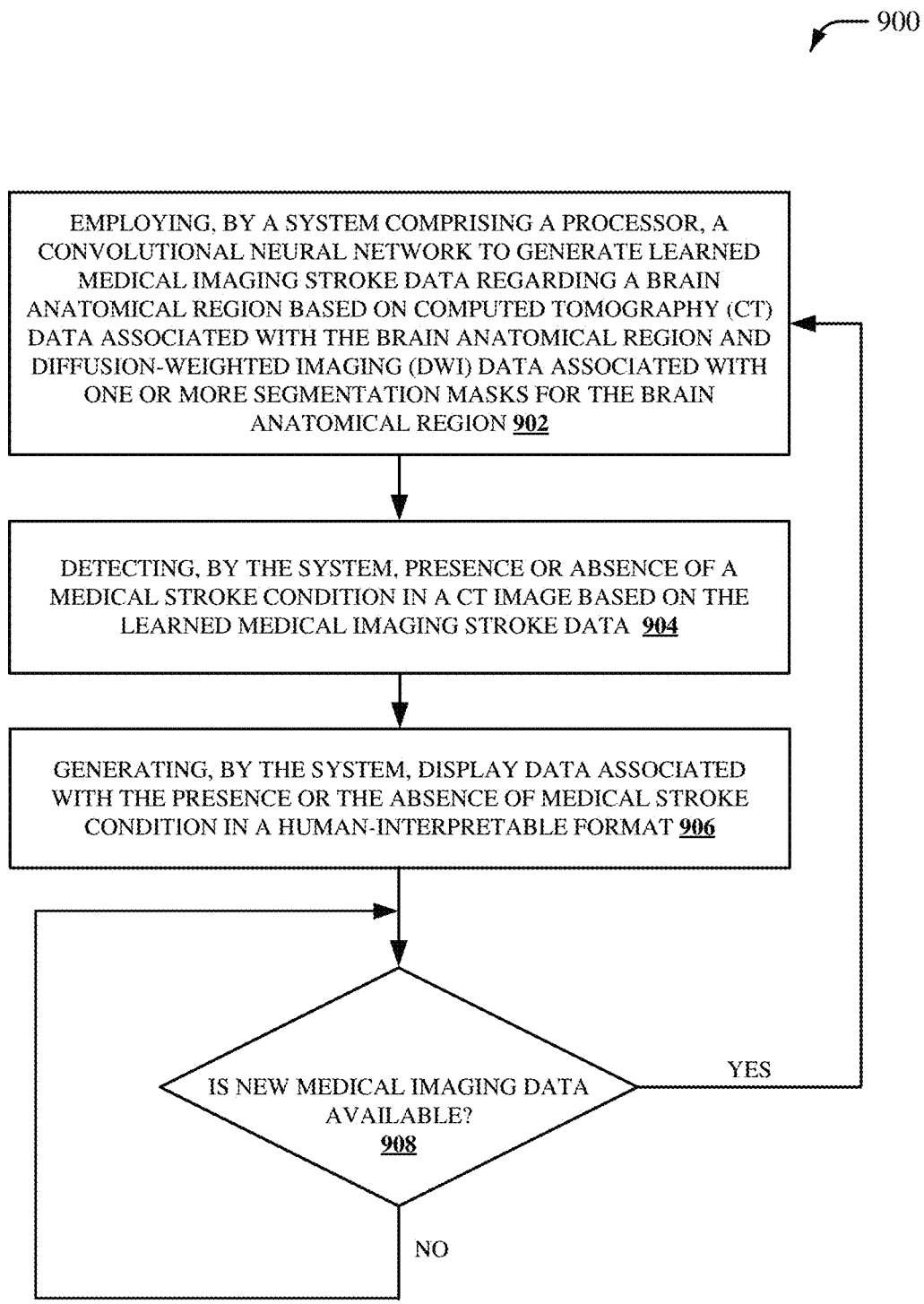
FIG. 9 depicts a flow diagram of an example method for generating and/or employing a computed tomography medical imaging stroke model, in accordance with one or more embodiments described herein.

FIG. 9 illustrates a flow diagram of an example, non-limiting computer-implemented method 900 for generating and/or employing a CT medical imaging stroke model in accordance with one or more embodiments described herein. Repetitive description of like elements employed in other embodiments described herein is omitted for sake of brevity. At 902, a convolutional neural network is employed, by a system comprising a processor (e.g., by the machine learning component 104), to generate learned medical imaging stroke data regarding a brain anatomical region based on computed tomography (CT) data associated with the brain anatomical region and diffusion-weighted imaging (DWI) data associated with one or more segmentation masks for the brain anatomical region. The CT data can include one or more CT images generated by one or more medical imaging devices. For example, the CT data 112 can include one or more CT images generated by one or more CT scanner devices. The one or more CT images of the CT data can be related to an anatomical region (e.g., a brain anatomical region) of one or more patient bodies. In aspect, a CT image included in the CT data can be a two-dimensional CT image or a three-dimensional CT image. In another aspect, the CT data can be a series of X-ray images captured via a set of X-ray detectors (e.g., a set of X-ray detects associated with a medical imaging device). The CT data can be received directly from one or more medical imaging devices. Alternatively, the CT data can be stored in one or more databases that receives and/or stores the CT data associated with the one or more medical imaging devices. In an embodiment, the CT data can include one or more NCCT images generated without use of contrast medication by a patient. The DWI data can include one or more one or more medical images generated by one or more medical imaging devices. For example, the DWI data can include one or more one or more medical images generated by one or more MRI scanner devices. In an aspect, a medical image included in the DWI data can be a DWI image that provides contrast based on a difference in a pattern of motion of water molecules with respect to the brain anatomical region of a patient body. For instance, a medical image included in the DWI data can be a DWI image that provides a measurement of a pattern of motion of water molecules within a voxel of the brain anatomical region. In another aspect, a medical image included in the DWI data can be associated with darkness information for the brain anatomical region. For instance, an amount of weighting for a parameter (e.g., a T1 parameter, a T2 parameter, etc.) employed to generate the DWI data can provide an increased degree of darkness in the DWI data. In yet another aspect, a medical image included in the DWI data can be a two-dimensional medical image or a three-dimensional medical image. For instance, the DWI data can be electromagnetic radiation imagery captured via a set of sensors (e.g., a set of sensors associated with a medical imaging device). In certain embodiments, the DWI data can be a series of electromagnetic radiation imagery captured via a set of sensors (e.g., a set of sensors associated with a medical imaging device) during an interval of time. The DWI data can be received directly from one or more medical imaging devices. Alternatively, the DWI data can be stored in one or more databases that receives and/or stores the DWI data associated with the one or more medical imaging devices. In one example, the DWI data can include one or more MRI DWI images. In certain embodiments, the CT data and the DWI data can both be acquired within a certain time frame (e.g., within 3 hours or less). For instance, the CT data can be acquired by one or more CT scanner devices. Furthermore, within a certain time frame (e.g., within 3 hours or less) after the CT data is acquired by the one or more CT scanner devices, the DWI data can be acquired by one or more MRI scanner devices. As such, improved correlation of the CT data and the DWI data for providing training data for a convolutional neural network can be achieved.

The learned medical imaging stroke data can be, for example, deep learning data related to a stroke medical condition for the brain anatomical region associated with the CT data. For instance, the learned medical imaging stroke data can classify and/or determine a location of a stroke for the brain anatomical region associated with the CT data. In an aspect, the convolutional neural network can analyze the CT data and the DWI data using deep learning and/or one or more machine learning techniques to generate the learned medical imaging stroke data. In an embodiment, the convolutional neural network can include a set of convolutional layers associated with upsampling and/or downsampling. Furthermore, in certain embodiments, the convolutional neural network can include a contracting path of convolutional layers and/or an expansive path of convolutional layers. In certain embodiments, the convolutional neural network can employ context data associated with previous inputs provided to the convolutional neural network and/or previous outputs provided by the convolutional neural network to analyze the CT data and the DWI data. In a non-limiting embodiment, the convolutional neural network can be an adapted U-net model for analyzing the CT data and the DWI data. For instance, the adapted U-net model can be a fully convolutional network that employs successive convolutional layers associated with downsampling followed by successive convolutional layers associated with upsampling. The adapted U-net model can also employ a segmentation loss function to modify one or more portions of the adapted U-net model. Additionally or alternatively, the adapted U-net model can employ a classification loss function to modify one or more portions of the adapted U-net model. In an embodiment, the convolutional neural network can be a medical imaging stroke model that is trained to classify and/or locate a medical stroke condition (e.g., the ischemic stroke condition, the infarct, etc.) with respect to the brain anatomical region.

At 904, presence or absence of a medical stroke condition in a CT image is determined, by the system (e.g., by the medical diagnosis component 106) based on the learned medical imaging stroke data. For example, presence or absence of an ischemic stroke condition associated with the CT image can be detected based on the learned medical imaging stroke data. The CT image can be a CT image generated by a medical imaging device. For example, the CT image can be a CT image generated by a CT scanner device. The CT image can be related to an anatomical region (e.g., a brain anatomical region) of a patient body scanned by the medical imaging device. For example, the CT image can be related to an anatomical region (e.g., a brain anatomical region) of a patient body scanned by the CT scanner device. In aspect, the CT image can be a two-dimensional CT image or a three-dimensional CT image. In another aspect, the CT image can be represented as a series of X-ray images captured via a set of X-ray detectors (e.g., a set of X-ray detects associated with a medical imaging device) of the medical imaging device (e.g., the CT scanner device). The CT image can be received directly from the medical imaging device (e.g., the CT scanner device). Alternatively, the CT image can be stored in one or more databases that receives and/or stores the CT image associated with the medical imaging device (e.g., the CT scanner device). In an embodiment, the CT image can be a NCCT image generated without use of contrast medication by the patient associated with the anatomical region (e.g., the brain anatomical region). In certain embodiments, presence or absence of an infarct associated with the CT image can be detected based on the learned medical imaging stroke data. The infarct can be an area of the brain anatomical region that satisfies a defined criterion associated with a necrosis medical condition. For instance, the infarct can be an area of necrosis of the brain anatomical region resulting from lack of blood supply to the brain anatomical region. Additionally, in another embodiment, determine a size of the medical stroke condition can be determined based on the learned medical imaging stroke data. For example, a size of the infarct can be determined based on the learned medical imaging stroke data. In an aspect, an outline of the area of the brain anatomical region associated with the infarct can be determined.

At 906, display data associated with the presence or the absence of medical stroke condition is generated, by the system (e.g., by the display component 202) in a human-interpretable format. In an example, the display data can be provided to a user device in a human-interpretable format. Additionally or alternatively, display data can be associated with the size of the medical stroke condition (e.g., the ischemic stroke condition, the infarct, etc.). In certain embodiments, the display data can include a multi-dimensional visualization associated the presence or the absence of the medical stroke condition (e.g., the ischemic stroke condition, the infarct, etc.). Additionally or alternatively, the display data can include a multi-dimensional visualization associated with the size of the medical stroke condition (e.g., the ischemic stroke condition, the infarct, etc.). The multi-dimensional visualization can be a graphical representation of the CT image and/or other medical imaging data that shows a classification and/or a location of the medical stroke condition (e.g., the ischemic stroke condition, the infarct, etc.) with respect to the brain anatomical region. In certain embodiments, a multi-dimensional visualization that overlays a segmentation associated with the medical stroke condition onto the CT image can be generated. In certain embodiments, medical image data and/or machine learning output can be provided to two or more users at two or more locations. Updates and/or interactions with machine learning outputs can also be managed through user interactions associated with two or more users at two or more locations.

At 908, it is determined whether new medical imaging data is available. If yes, the computer-implemented method 900 returns to 902. If no, the computer-implemented method 900 returns to 908 to further determine whether new medical imaging data is available. In certain embodiments, the computer-implemented method 900 can additionally or alternatively include transforming, by the system (e.g., by the machine learning component 104), the one or more segmentation masks associated with the DWI data to match an orientation of the CT data. In certain embodiments, the computer-implemented method 900 can additionally or alternatively include providing, by the system (e.g., by the machine learning component 104), the CT data and a transformed version of the one or more segmentation masks to the convolutional neural network For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Moreover, because at least employing a convolutional neural network, etc. is established from a combination of electrical and mechanical components and circuitry, a human is unable to replicate or perform processing performed by the medical imaging component 102 (e.g., the machine learning component 104, the medical diagnosis component 106 and/or the display component 202) disclosed herein. For example, a human is unable to perform machine learning associated with a convolutional neural network, etc.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 10:
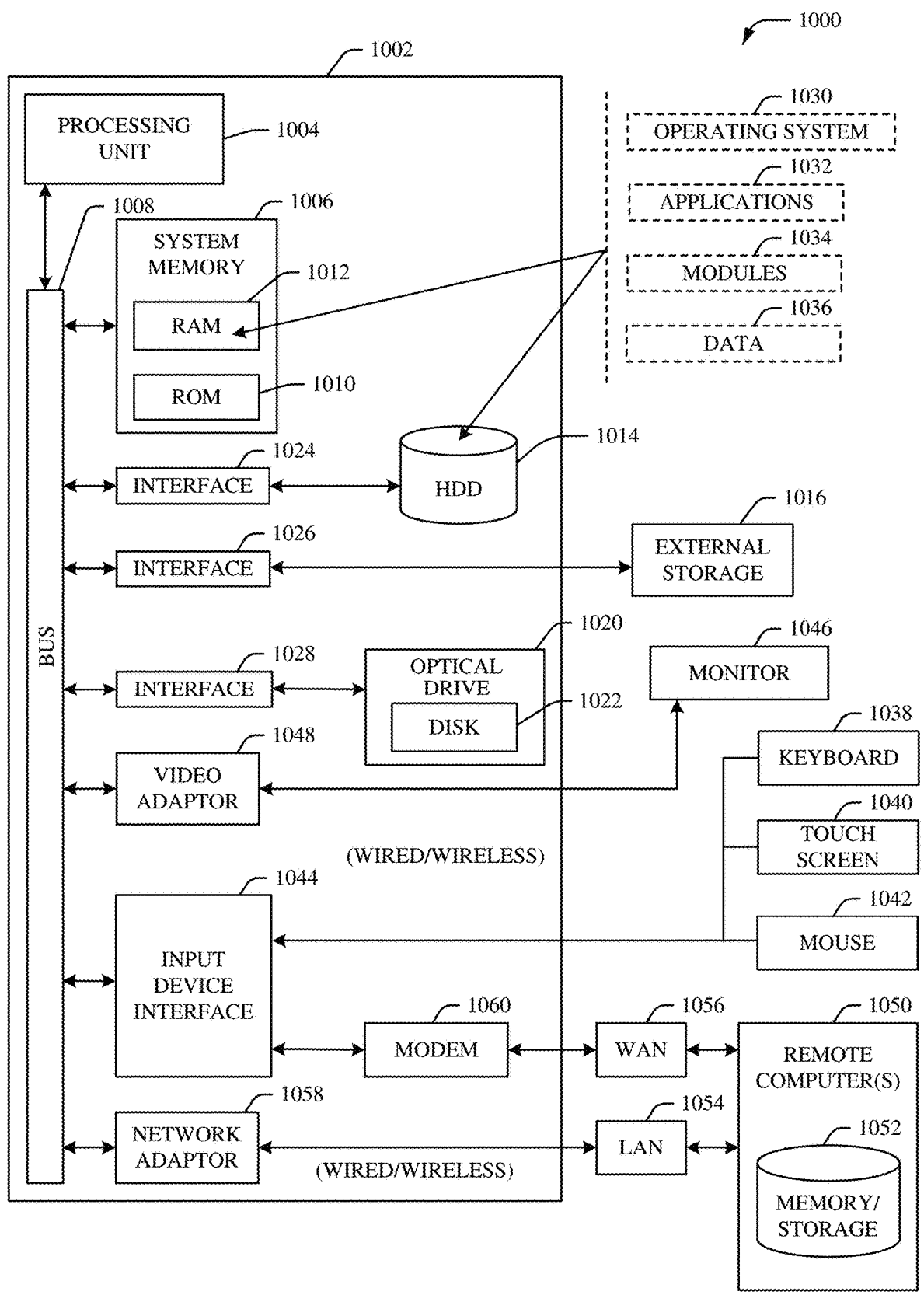
FIG. 10 is a schematic block diagram illustrating a suitable operating environment.

In order to provide additional context for various embodiments described herein, FIG. 10 and the following discussion are intended to provide a brief, general description of a suitable computing environment 1000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 10, the example environment 1000 for implementing various embodiments of the aspects described herein includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures can also be employed as the processing unit 1004.

The system bus 1008 can be any of several types of bus structure that can further interconnect to a memory bus (with or without a memory controller), a peripheral bus, and a local bus using any of a variety of commercially available bus architectures. The system memory 1006 includes ROM 1010 and RAM 1012. A basic input/output system (BIOS) can be stored in a non-volatile memory such as ROM, erasable programmable read only memory (EPROM), EEPROM, which BIOS contains the basic routines that help to transfer information between elements within the computer 1002, such as during startup. The RAM 1012 can also include a high-speed RAM such as static RAM for caching data.

The computer 1002 further includes an internal hard disk drive (HDD) 1014 (e.g., EIDE, SATA), one or more external storage devices 1016 (e.g., a magnetic floppy disk drive (FDD) 1016, a memory stick or flash drive reader, a memory card reader, etc.) and an optical disk drive 1020 (e.g., which can read or write from a CD-ROM disc, a DVD, a BD, etc.). While the internal HDD 1014 is illustrated as located within the computer 1002, the internal HDD 1014 can also be configured for external use in a suitable chassis (not shown). Additionally, while not shown in environment 1000, a solid state drive (SSD) could be used in addition to, or in place of, an HDD 1014. The HDD 1014, external storage device(s) 1016 and optical disk drive 1020 can be connected to the system bus 1008 by an HDD interface 1024, an external storage interface 1026 and an optical drive interface 1028, respectively. The interface 1024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. The systems and methods described herein can be implemented utilizing various commercially available operating systems or combinations of operating systems.

Computer 1002 can optionally comprise emulation technologies. For example, a hypervisor (not shown) or other intermediary can emulate a hardware environment for operating system 1030, and the emulated hardware can optionally be different from the hardware illustrated in FIG. 10. In such an embodiment, operating system 1030 can comprise one virtual machine (VM) of multiple VMs hosted at computer 1002. Furthermore, operating system 1030 can provide runtime environments, such as the Java runtime environment or the .NET framework, for applications 1032. Runtime environments are consistent execution environments that allow applications 1032 to run on any operating system that includes the runtime environment. Similarly, operating system 1030 can support containers, and applications 1032 can be in the form of containers, which are lightweight, standalone, executable packages of software that include, e.g., code, runtime, system tools, system libraries and settings for an application.

Further, computer 1002 can be enable with a security module, such as a trusted processing module (TPM). For instance with a TPM, boot components hash next in time boot components, and wait for a match of results to secured values, before loading a next boot component. This process can take place at any layer in the code execution stack of computer 1002, e.g., applied at the application execution level or at the operating system (OS) kernel level, thereby enabling security at any level of code execution.

A user can enter commands and information into the computer 1002 through one or more wired/wireless input devices, e.g., a keyboard 1038, a touch screen 1040, and a pointing device, such as a mouse 1042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1004 through an input device interface 1044 that can be coupled to the system bus 1008, but can be connected by other interfaces, such as a parallel port, an IEEE 1394 serial port, a game port, a USB port, an IR interface, a BLUETOOTH® interface, etc.

A monitor 1046 or other type of display device can be also connected to the system bus 1008 via an interface, such as a video adapter 1048. In addition to the monitor 1046, a computer typically includes other peripheral output devices (not shown), such as speakers, printers, etc.

The computer 1002 can operate in a networked environment using logical connections via wired and/or wireless communications to one or more remote computers, such as a remote computer(s) 1050. The remote computer(s) 1050 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1052 is illustrated. The logical connections depicted include wired/wireless connectivity to a local area network (LAN) 1054 and/or larger networks, e.g., a wide area network (WAN) 1056. Such LAN and WAN networking environments are commonplace in offices and companies, and facilitate enterprise-wide computer networks, such as intranets, all of which can connect to a global communications network, e.g., the Internet.

When used in a LAN networking environment, the computer 1002 can be connected to the local network 1054 through a wired and/or wireless communication network interface or adapter 1058. The adapter 1058 can facilitate wired or wireless communication to the LAN 1054, which can also include a wireless access point (AP) disposed thereon for communicating with the adapter 1058 in a wireless mode.

When used in a WAN networking environment, the computer 1002 can include a modem 1060 or can be connected to a communications server on the WAN 1056 via other means for establishing communications over the WAN 1056, such as by way of the Internet. The modem 1060, which can be internal or external and a wired or wireless device, can be connected to the system bus 1008 via the input device interface 1044. In a networked environment, program modules depicted relative to the computer 1002 or portions thereof, can be stored in the remote memory/storage device 1052. It will be appreciated that the network connections shown are example and other means of establishing a communications link between the computers can be used.

When used in either a LAN or WAN networking environment, the computer 1002 can access cloud storage systems or other network-based storage systems in addition to, or in place of, external storage devices 1016 as described above. Generally, a connection between the computer 1002 and a cloud storage system can be established over a LAN 1054 or WAN 1056 e.g., by the adapter 1058 or modem 1060, respectively. Upon connecting the computer 1002 to an associated cloud storage system, the external storage interface 1026 can, with the aid of the adapter 1058 and/or modem 1060, manage storage provided by the cloud storage system as it would other types of external storage. For instance, the external storage interface 1026 can be configured to provide access to cloud storage sources as if those sources were physically connected to the computer 1002.

The computer 1002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 11:
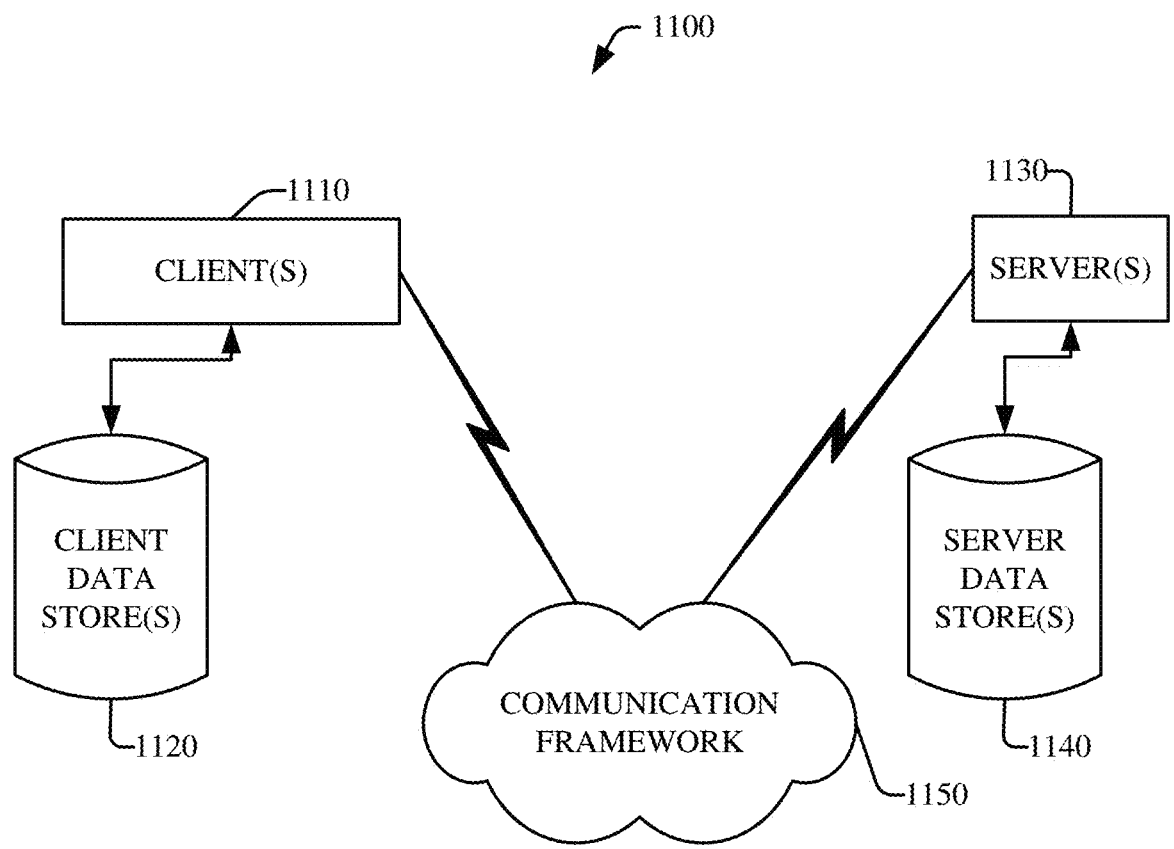
FIG. 11 is a schematic block diagram of a sample-computing environment.

FIG. 11 is a schematic block diagram of a sample-computing environment 1100 with which the subject matter of this disclosure can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing this disclosure, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. The client(s) 1110 are operatively connected to one or more client data store(s) 1120 that can be employed to store information local to the client(s) 1110. Similarly, the server(s) 1130 are operatively connected to one or more server data store(s) 1140 that can be employed to store information local to the servers 1130.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
   a memory that stores computer executable components; and
   a processor that executes computer executable components stored in the memory, wherein the computer executable components comprise:
      a machine learning component that employs a convolutional neural network to generate learned medical imaging stroke data regarding a brain anatomical region based on computed tomography (CT) data associated with the brain anatomical region and diffusion-weighted imaging (DWI) data associated with one or more segmentation masks for the brain anatomical region and transforms the one or more segmentation masks associated with the DWI data to match an orientation of the CT data; and
      a medical diagnosis component that detects presence or absence of a medical stroke condition in a CT image based on the learned medical imaging stroke data.

2. The system of claim 1, wherein the machine learning component provides the CT data and a transformed version of the one or more segmentation masks to the convolutional neural network.

3. The system of claim 1, wherein the medical diagnosis component detects presence or absence of an ischemic stroke condition associated with the CT image based on the learned medical imaging stroke data.

4. The system of claim 1, wherein the medical diagnosis component generates a contour mask associated with the medical stroke condition based on the learned medical imaging stroke data.

5. The system of claim 1, wherein the medical diagnosis component determines a size of an ischemic stroke condition associated with the CT image based on the learned medical imaging stroke data.

6. The system of claim 1, further comprising:
a display component that generates display data associated with the presence or the absence of the medical stroke condition in a human-interpretable format.

7. The system of claim 6, wherein the display component generates a multi-dimensional visualization associated with the presence or the absence of the medical stroke condition.

8. The system of claim 7, wherein the display component overlays a segmentation associated with the medical stroke condition onto the CT image.

9. A method, comprising:
employing, by a system comprising a processor, a convolutional neural network to generate learned medical imaging stroke data regarding a brain anatomical region based on computed tomography (CT) data associated with the brain anatomical region and diffusion-weighted imaging (DWI) data associated with one or more segmentation masks for the brain anatomical region;
transforming, by the system, the one or more segmentation masks associated with the DWI data to match an orientation of the CT data; and
detecting, by the system, presence or absence of a medical stroke condition in a CT image based on the learned medical imaging stroke data.

10. The method of claim 9, further comprising:
providing, by the system, the CT data and a transformed version of the one or more segmentation masks to the convolutional neural network.

11. The method of claim 9, wherein the detecting comprises detecting presence or absence of an ischemic stroke condition associated with the CT image based on the learned medical imaging stroke data.

12. The method of claim 9, further comprising:
determining, by the system, a size of an ischemic stroke condition associated with the CT image based on the learned medical imaging stroke data.

13. The method of claim 9, further comprising:
generating, by the system, display data associated with the presence or the absence of medical stroke condition in a human-interpretable format.

14. The method of claim 9, further comprising:
generating, by the system, a multi-dimensional visualization that overlays a segmentation associated with the medical stroke condition onto the CT image.

15. A non-transitory computer readable storage device comprising instructions that, in response to execution, cause a system comprising a processor to perform operations, comprising:
generating, using a convolutional neural network, learned medical imaging stroke data regarding a brain anatomical region based on computed tomography (CT) data associated with the brain anatomical region and diffusion-weighted imaging (DWI) data associated with one or more segmentation masks for the brain anatomical region;
transforming the one or more segmentation masks associated with the DWI data to match an orientation of the CT data; and
detecting presence or absence of a medical stroke condition associated with a CT image based on the learned medical imaging stroke data.

16. The non-transitory computer readable storage device of claim 15, wherein the operations further comprise:
providing the CT data and a transformed version of the one or more segmentation masks to the convolutional neural network.

17. The non-transitory computer readable storage device of claim 15, wherein the operations further comprise:
generating a multi-dimensional visualization that overlays a segmentation associated with the medical stroke condition onto the CT image.

* * * * *